US007142927B2

(12) United States Patent
Benser et al.

(10) Patent No.: US 7,142,927 B2
(45) Date of Patent: Nov. 28, 2006

(54) METHOD AND SYSTEM FOR THE SELECTION OF CARDIAC DEFIBRILLATION SHOCKS BASED ON DISCOMFORT

(75) Inventors: Michael E. Benser, Sylmar, CA (US); Raymond E. Ideker, Birmingham, AL (US); Milton M. Morris, Minneapolis, MN (US)

(73) Assignee: UAB Research Foundation, Birmingham, AL (US)

( * ) Notice: Subject to any disclaimer, the term of this patent is extended or adjusted under 35 U.S.C. 154(b) by 642 days.

(21) Appl. No.: 10/234,624

(22) Filed: Sep. 4, 2002

(65) Prior Publication Data

US 2004/0044370 A1    Mar. 4, 2004

(51) Int. Cl.
   *A61N 1/39* (2006.01)
(52) U.S. Cl. ............................................. 607/63; 607/7
(58) Field of Classification Search .................... 607/7, 607/8, 63
   See application file for complete search history.

(56) References Cited

U.S. PATENT DOCUMENTS

| 5,165,403 | A |   | 11/1992 | Mehra ........................ 128/419 |
| 5,184,616 | A | * | 2/1993 | Weiss ............................. 607/4 |
| 5,830,236 | A | * | 11/1998 | Mouchawar et al. ........... 607/5 |
| 5,978,705 | A |   | 11/1999 | KenKnight et al. ............. 607/5 |
| 6,275,730 | B1 |   | 8/2001 | KenKnight et al. ............. 607/5 |
| 6,298,266 | B1 | * | 10/2001 | Rubin et al. .................... 607/5 |
| 6,327,500 | B1 | * | 12/2001 | Cooper et al. .................. 607/5 |

OTHER PUBLICATIONS

SoRelle R. Atrial fibrillation will increase 2.5 times over next 50 years with aging population. Circulation. 2001;103(20):E9043-9044.

Sundt TM, Camillo C,. Cox JL. The maze procedure for cure of atrial fibrillation. Cardiol Clin. 1997;15(4):739-748.

Shah DC, Haissaguerre M, Jais P, Hocini M, Yamane T, Deisenhofer I, Garrigue S, Clementy J. Electrophysiologically guided ablation of the pulmonary veins for the curative treatment of atrial fibrillation. Ann Med. 2000;32(6):408-416.

Kerber RE. Transthoracic cardioversion of atrial fibrillation and flutter: standard techniques and new advances. Am J Cardiol. 1996;78(8A):22-26.

Alt E, Schmitt C, Ammer R, Coenen M, Fotuhi P, Karch M, Blasini R: Initial experience with intracardiac atrial defibrillation in patients with chronic atrial fibrillation. Pac Clin Electrophysiol. 1994;17(5 Pt 2):1067-1078.

Alt E, Ammer R, Schmitt C, Evans F, Lehmann G, Pasquantonio J, Schomig A: A comparison of treatment of atrial fibrillation with low-energy intracardiac cardioversion and conventional external cardioversion. Eur Heart J 1997;18(11):1796-1804.

(Continued)

*Primary Examiner*—George Manuel
*Assistant Examiner*—Nicole R. Kramer
(74) *Attorney, Agent, or Firm*—Myers Bigel Sibley & Sajovec

(57) ABSTRACT

Methods, systems and computer program products for selecting a shock profile for a defibrillator based on patient discomfort to a plurality of different defibrillating shocks include delivering a first defibrillating shock having an associated first shock profile to a patient, and measuring the associated physical displacement of a selected region in the patient. A second defibrillating shock having an associated second shock profile is delivered to the patient, and the associated physical displacement of the selected region in measured. One of the first or second shock profiles is selected based on which shock profile has the lesser amount of measured physical displacement.

42 Claims, 16 Drawing Sheets

OTHER PUBLICATIONS

Wellens HJ, Lau CP, Luderitz B, Akhtar M, Waldo AL, Camm AJ, Timmermans C, Tse HF, Jung W, Jordaens L, Ayers G: Atrioverter: an implantable device for the treatment of atrial fibrillation. Circulation 1998;98:1651-165.

Jung W, Wolpert C, Esmailzadeh B, Spehl S, Herwig S, Schumacher B, Lewalter T, Omran H, Schimpf R, Vahlhaus C, Welz A, Luderitz B: Clinical experience with implantable atrial and combined atrioventricular defibrillators. J. Intervent Cardiac Electrophysiol 2000;4(Suppl 1):185-195.

Daoud EG, Timmermans C, Fellows C, Hoyt R, Lemery R, Dawson K, Ayers GM. Initial clinical experience with ambulatory use of an implantable atrial defibrillator for conversion of atrial fibrillation. Metrix Investigators. Circulation. 2000;102(12):1407-1413.

Schoels W, Swerdlow CD, Jung W, Stein KM, Seidl K, Haffajee CJ. Worldwide clinical experience with a new dual-chamber implantable cardioverter defibrillator system. J Cardiovasc Electrophysiol. 2001;12 (5):521-528.

Heisel A, Jung J: The atrial defibrillator: a stand-alone device or part of a combined dual-chamber system? Am J Cardiol 1999;83:218D-226D.

Tse HF, Lau CP. Impantable atrioventricular defibrillators. Cardiac Electrophysiol Rev 2001;5:24-30.

Lok NS, Lau CP, Tse HF, Ayers GM: Clinical shock tolerability and effect of different right atrial electrode locations on efficacy of low energy human transvenous atrial defibrillation using an implantable lead system. J Am Coll Cardiol 1997;30(5):1324-1330.

Levy S, Ricard P, Gueunoun M, Yapo F, Trigano J, Mansouri C, Paganelli F. Low-energy cardioversion of spontaneous atrial fibrillation. Immediate and long-term results. Circulation. 1997;96(1):253-259.

Murgatroyd FD, Slade AKB, Sopher SM, Rowland E, Ward DE, Camm AJ: Efficacy and tolerability of transvenous low energy cardioversion of paroxysmal atrial fibrillation in humans. J Am Coll Cardiol 1995;25:1347-1353.

Harbinson MT, Imam Z, McEneaney DJ, Trouton TG, Burgess L, Ayers GM, Ripley K, Dempsey G, Anderson J, Adgey AAJ: Patient discomfort after transvenous catheter cardioversion of atrial tachyarrhythmias with rounded waveforms—initial results. (Abstract) Circulation 1996; 94(8):I-67.

Jung W, Pfeiffer D, Wolpert C, Pizzulli L, Fehske W, Schumacher B, Lewalter T, Omran H, Korte T, Luderitz B: Which patients do benefit from an implantable atrial defibrillator? (Abstract) J Am Coll Cardiol 1996;27(2, suppl. A):301A-302A.

Tomassoni G, Newby KH, Kearney MM, Brandon MJ, Barold H, Natale A. Testing different biphasic waveforms and capacitances: effect on atrial defibrillation threshold and pain perception. J. Am Coll. Cardiol. 1996; 28(3):695-699.

Sheppard RC, K Miller, J Reddinger, R Henderson. Even the lowest energy ICD shocks hurt. Europace Supplements. 2000;1:A25.

Jung J, Heisel A, Fries R, Kollner V: Tolerability of internal low-energy shock strengths currently needed for endocardial atrial cardioversion. Am J Cardiol 1997; 80(11):1489-1490.

Steinhaus DM, Cardinal D, Mongeon L, Mattson L, Waters M, Foley L, Corrigan S: Atrial defibrillation: are low energy shocks acceptable to patients? (Abstract) Pac Clin Electrophysiol 1996;19(Part 2):625.

Cooper RA, Alferness CA, Smith WM, Ideker RE: Internal cardioversion of atrial fibrillation in sheep. Circulation 1993;87(5):1673-1686.

Cooper RA, Smith WM, Ideker RE: Internal cardioversion of atrial fibrillation: marked reduction in defibrillation threshold with dual current pathways. Circulation 1997;96(8):2693-2700.

Cooper RA, Plumb VJ, Epstein AE, Kay GN, Ideker RE: Marked reduction in internal atrial defribillation thresholds with dual-current pathways and sequential shocks in humans. Circulation 1998;97(25)2527-2535.

Zheng X, Benser ME, Walcott GP, Girouard SD, Rollins DL, Smith WM, Ideker RE. Reduction of atrial defibrillation threshold with an interatrial septal electrode. Circulation 2000;102:2659-2664.

Lok et al.; "Clinical Shock Tolerability and Effect of Different Right Atrial Electrode Locations on Efficacy of Low Energy Human Transvenous Atrial Defibrillation Using an Implantable Lead System", *JACC* 30:5 1324-1330 (1997).

Neri et al.; "Internal Cardioversion of Chronic Atrial Fibrillation in Patients", *PACE* 20 2237-2242 (1997).

Prof. Dr. med. Eckhard Alt; "Letters to the Editor", *PACE* 21 633-634 (1998).

* cited by examiner

METHOD AND SYSTEM FOR THE SELECTION OF CARDIAC DEFIBRILLATION SHOCKS BASED ON DISCOMFORT

FIELD OF THE INVENTION

The present invention concerns methods and systems that may reduce patient discomfort associated with therapeutic cardiac shocks.

BACKGROUND OF THE INVENTION

Atrial fibrillation is one of the most common cardiac arrhythmia. Atrial fibrillation is a debilitating disease that afflicts 20 million people worldwide. Health consequences associated with atrial fibrillation include decreased cardiac output, less regular ventricular rhythm, the formation of blood clots in the atrial appendages, and an increased incidence of stroke. While some drugs are available for the treatment of atrial fibrillation, they have a number of side effects which reduce their therapeutic utility. The use of atrial counter shocks remain one of the primary treatments for atrial fibrillation.

Unlike patients afflicted with ventricular fibrillation, patients afflicted with atrial fibrillation are conscious. The pain associated with the administration of the defibrillation shock can be severe, and there is a need to reduce the pain to the patient being treated while maintaining clinical efficacy of the defibrillation shock. Internal, catheter-based atrial defibrillation has been found to increase efficacy while requiring lower shock strength in comparison to traditional transthoracic cardioversion. Implantable devices for internal catheter-based atrial defibrillation have been developed and are being clinically investigated. However, the clinical acceptance of implantable atrial defibrillation devices may be limited by the discomfort associated with the atrial defibrillation shocks. Other fibrillation-based treatments in which pain may be experienced by the patient include the treatmentment of hemodynamically stable ventricular tachycardia.

Furthermore, pain and discomfort are difficult to quantify in an absolute measurement. One method for estimating pain is to ask patients to rate the pain that they experience. This method depends on the subjectivity of the patient, and therefore, it is difficult to compare the assessment of pain reported from one patient with the assessment of pain reported from other patients. The difficulties and inaccuracies in measuring pain and discomfort complicate the problem of minimizing pain in various types of treatments, including atrial defibrillation.

Systems and methods proposed that deliver atrial defibrillation include U.S. Pat. No. 5,165,403 to R. Mehra ("Mehra"), the contents of which are hereby incorporated by reference as if recited in full herein. Mehra discloses an implantable lead system useful for defibrillating (or "cardioverting") the atria of a patient's heart. In the disclosed system, one electrode is positioned in either the great cardiac vein or coronary sinus of the heart, and another electrode is positioned in either the right atrium or superior vena cava of the heart.

U.S. Pat. No. 6,327,500 to Cooper et al., the contents of which are hereby incorporated by reference as if recited in full herein, discloses an implantable system for defibrillation of the atria of a patient's heart. A pulse generator delivers a second atrial defibrillation pulse after a first defibrillation pulse without intervening monitoring thereof to reduce the voltage necessary for the shock.

U.S. Pat. Nos. 5,978,705 and 6,275,730, both to KenKnight et al., the contents of which are hereby incorporated by reference as if recited in full herein, each disclose an implantable system for the defibrillation or cardioversion of the heart comprising a plurality of primary electrodes, a power supply, and a control circuit. The primary electrodes are configured for delivering a cardiversion pulse along a predetermined current pathway in a first portion of the heart where the current pathway defines a weak field area in a second portion of the heart.

However, there remains a need for measuring and/or reducing the discomfort and pain associated with shocks for treating atrial fibrillation, hemodynamically stable ventricular tachycardia, and other conditions in which discomfort and pain may be problematic.

SUMMARY OF THE INVENTION

Embodiments of the present invention provide methods, systems and computer program products for selecting a shock profile for defibrillation based on the determined patient discomfort to a plurality of different defibrillating shock profiles. In particular embodiments of the invention a first defibrillating shock having a first shock profile is delivered to a patient and the physical displacement of a selected region in the patient associated with the first shock is measured. A second defibrillating shock having an associated second shock profile is delivered to the patient, and the physical displacement associated with the second shock is measured. One of the first or second shock profiles is selected based on which shock profile has the lesser amount of measured physical displacement.

In certain embodiments of the invention, the measurement of physical displacement includes measuring peak thoracic acceleration, for example, using a motion sensor such as an accelerometer.

Embodiments of the invention also provide a computer program product for assessing patient discomfort associated with selected defibrillation shocks. In certain embodiments, the computer program product includes a computer readable storage medium having computer readable program code embodied in the medium. The computer-readable program code includes code that obtains data associated with the physical displacement of the body of a subject in response to administration of a first defibrillation shock having an associated first shock profile, code that obtains data associated with the physical displacement of the body of a subject in response to administration of a second defibrillation shock having an associated second shock profile, and code that compares the data associated with the physical displacements for the first and second shocks. In certain embodiments, the computer program product further includes code that selects one of the first or second shock profiles based on which profile has the lesser amount of physical displacement.

Other embodiments of the invention are directed defibrillator systems that include an implantable housing, a power source held in the housing, a controller held in the housing operatively associated with the power source, and a shock generator held in the housing operatively associated with the power source and the controller. The shock generator is configured to deliver a plurality of different selectable shock profiles, each having a respective predetermined shock strength, waveform, and shock vector. Computer readable program code is operatively associated with the controller for determining body displacement to estimate patient discomfort during the delivery of selected defibrillating shock profiles.

The foregoing and other objects and aspects of the present invention are explained in greater detail in the drawings herein and the specification below.

DETAILED DESCRIPTION OF EMBODIMENTS OF THE INVENTION

Figure 1:
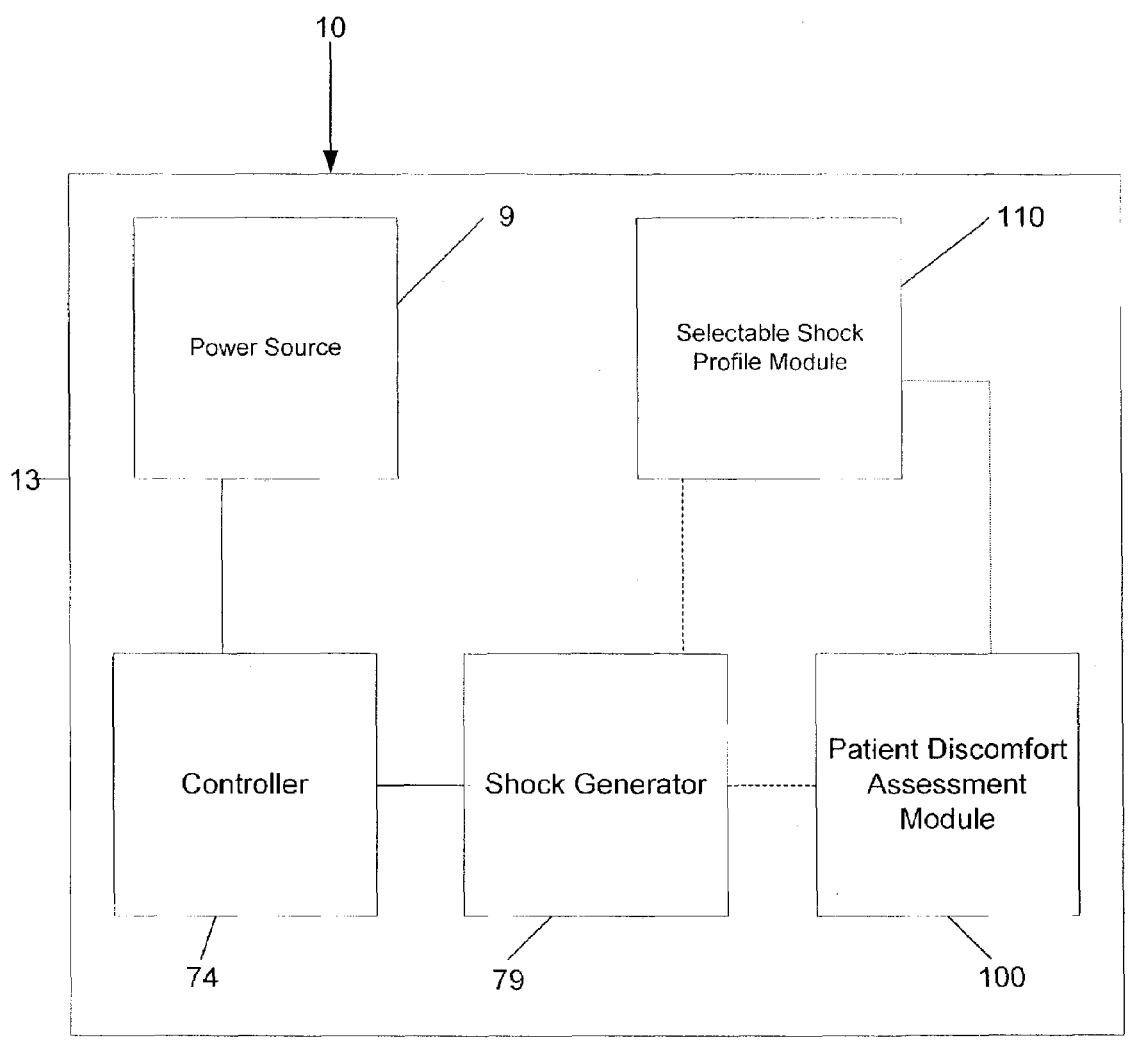
FIG. 1 is a schematic illustration of operational circuitry according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain regions, components, features or layers may be exaggerated for clarity. Broken lines where used indicate optional features, components or operations.

The flowcharts and block diagrams of certain of the figures herein illustrate the architecture, functionality, and operation of possible implementations for reducing patient discomfort according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved. In addition, some functions noted in the blocks may be combined or separated.

The present invention may be used to treat all forms of cardiac tachyarrhythmias, including atrial and ventricular fibrillation, with defibrillation (including cardioversion) shocks or pulses. Examples include treatment of polymorphic ventricular tachycardia, monomorphic ventricular tachycardia, ventricular fibrillation, atrial flutters, and atrial fibrillation. The present invention is particularly useful for treating cardioversion or defibrillation of atrial fibrillation or flutter or hemodynamically stable ventricular tachycardia and other conditions in which patient discomfort may be a therapeutic consideration and/or barrier to the clinical acceptance of treatment.

Typically, the issue of shock discomfort is not as great for ventricular defibrillation because ventricular defibrillation is usually immediately life-threatening and often renders the patient unconscious. However, in cases of cardioversion or defibrillation of atrial fibrillation or flutter or hemodynamically stable ventricular tachyardia, the rhythms are not usually immediately life-threatening, and many patients experience these rhythms with relatively frequent occurrences and are often conscious when they occur. Therefore, patient acceptance of therapy involving implantable device-based cardioversion/defibrillation may be limited by patient discomfort associated with defibrillation shocks.

Without wishing to be limited to any particular theory of the invention, it is presently believed that discomfort to shocks may be divided into three non-mutually exclusive components: 1) discomfort arising from the direct excitation of pain fibers; 2) discomfort arising directly and indirectly as a consequence of the resultant displacements; and 3) discomfort associated with psychological issues, including anxiety. It is presently believed that measurements of displacement may account for the first two components of shock discomfort. That is, displacement may be used as a proxy for shock discomfort levels. More specifically, one method to measure displacement includes the measurements of peak thoracic acceleration, for example, with an accelerometer. Other measurements or combination of measurements of shock-induced motion may also be used, for example, total displacement, scalar and non-scalar velocity, displacement, and acceleration measurements, integral measurements of scalar acceleration, and derivative measurements of acceleration (i.e., the rate at which acceleration changes). The measurement of displacement may be made with respect to the thorax or may include displacement measurements of other selected regions in the patient. The selected region may include any portion of the patient's body including substantially the entire body. Displacement may be measured by measuring changes in distance and/or displacement and/or the rate of change in distance of at least one selected region of the patient. Measurements of displacement may be made using conventional one-, two- or three- dimensional accelerometers.

In particular, it is presently believed that thoracic acceleration may be a good approximation for displacement and the resulting pain. Neuronal pain fibers lay within nerve tracts within the thorax. These same tracts house motor neuron axons. While these two types of neuronal axons have different characteristics and therefore different stimulation thresholds, it is believed that that large electrical shocks that stimulate one may also stimulate the other. Thus, thoracic skeletal muscle contraction via efferent innervating motor axon stimulation may approximate the direct stimulation of adjacent pain fibers, and/or any resulting discomfort. Displacement such as thoracic acceleration also may approximate any discomfort arising due directly to the trauma associated displacement response to shocks.

It is also believed that the physical discomfort associated with a particular shock may be related to the shock profile. As used herein, a "shock profile" is the defining characteristics of the shock and may include, for example, parameters relating to a particular electrode configuration, shock vector, peak voltage, the waveform, waveform mean, tilt, polarity, the number of pulses, delays between shocks, and any other characteristic describing a shock or shock sequence. As used herein, a "shock" having a specified "shock profile" may include one defibrillation pulse or a plurality of pulses grouped together.

Referring to FIG. 1, an exemplary atrial defibrillator 10 is shown. The atrial defibrillator 10 includes a implantable housing 13, a power source 9 held in the housing 13, and a controller 74 held in the housing 13 and operatively associated with the power source 9. A shock generator 79 is held in the housing and operatively associated with the power source and the controller. The shock generator 79 is configured to selectively deliver a plurality of different selectable shock profiles. A computer readable program code module 100 is operatively associated with the controller for determining patient physical displacement to estimate patient discomfort during the delivery of selected shock profiles. The measurement of displacement is made during or proximate delivery of the shock or after the shock time.

In certain embodiments, methods of selecting a shock profile for a defibrillator based on patient discomfort to a plurality of different defibrillating shocks can include delivering a first defibrillating shock having an associated first shock profile to a patient. The physical displacement of a selected region in the patient associated with the first shock during the first delivering step is measured. A second defibrillating shock having an associated second shock profile is delivered to the patient. The physical displacement of the selected region of the patient associated with the second shock during the second delivering step is then measured. One of the first or second shock profiles is selected, depending on which has the lesser amount of measured physical displacement at the respective atrial defibrillation threshold. The physical displacement may be measured by displacement sensors known to those of skill in the art such as one-, two-, or three-dimensional accelerometers. The displacement sensor may be situated subcutaneously or pericutaneously, and placed either externally on the patient's body or internally implanted. For example, the displacement sensor may be implanted in the thoracic cavity. In addition, a therapeutic agent may be administered proximate to and/or before the delivery of the shock. Suitable therapeutic agents are known to those of skill in the art and include agents for lowering the atrial defibrillation threshold and/or improving the efficiency of the shock. Examples of therapeutic agents include ibutilide, flecainide, and sedatives.

While the present invention is illustrated in certain of the figures, for example, with reference to particular divisions of programs, functions and memories, the present invention should not be construed as limited to such logical divisions. Thus, the present invention should not be construed as limited to the configuration of operation as shown in FIGS. 2 and 3 but is intended to encompass any configuration capable of carrying out the operations described herein.

Figure 2:
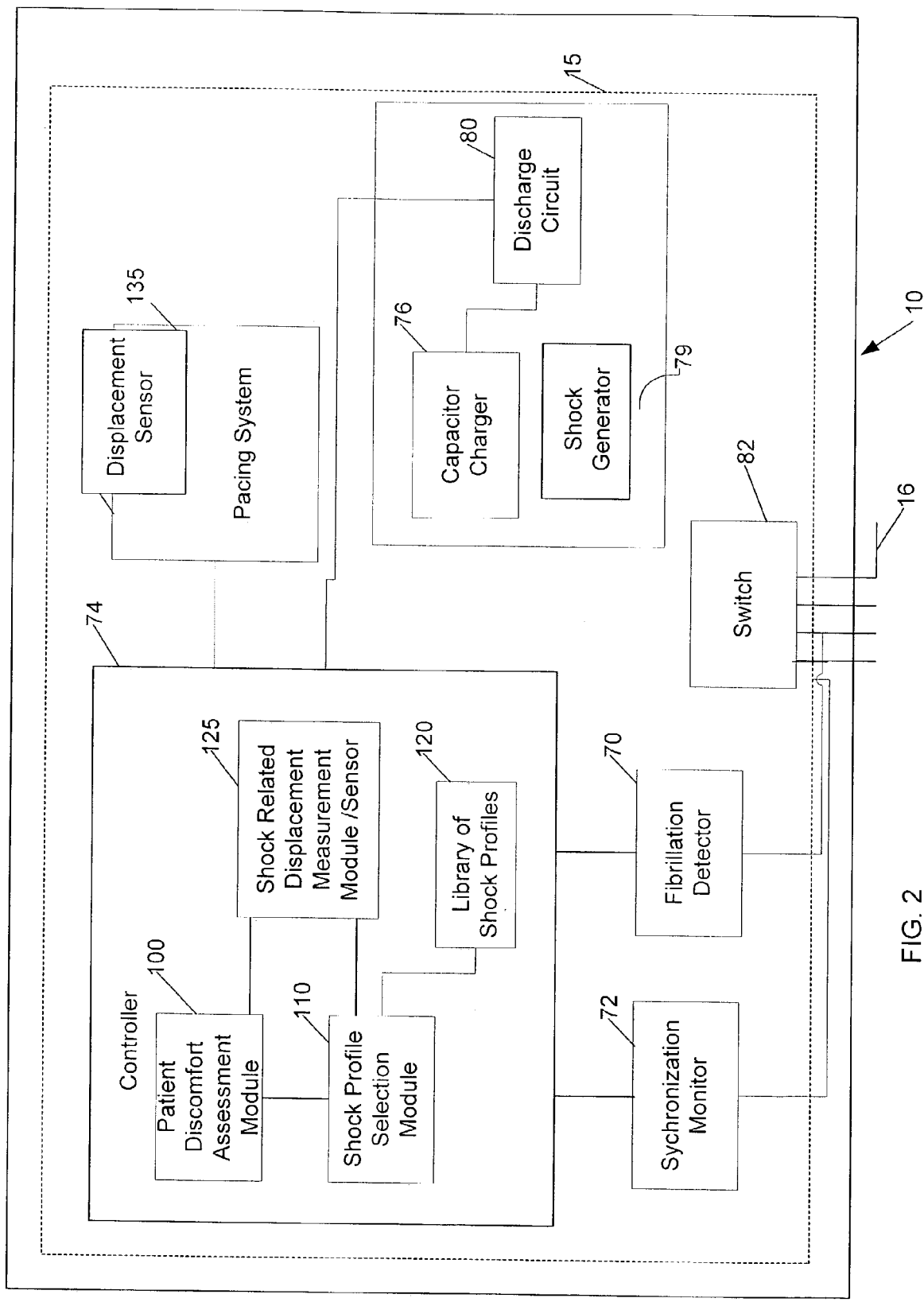
FIG. 2 is a schematic illustration of operational circuitry according to embodiments of the present invention
Figure 3:
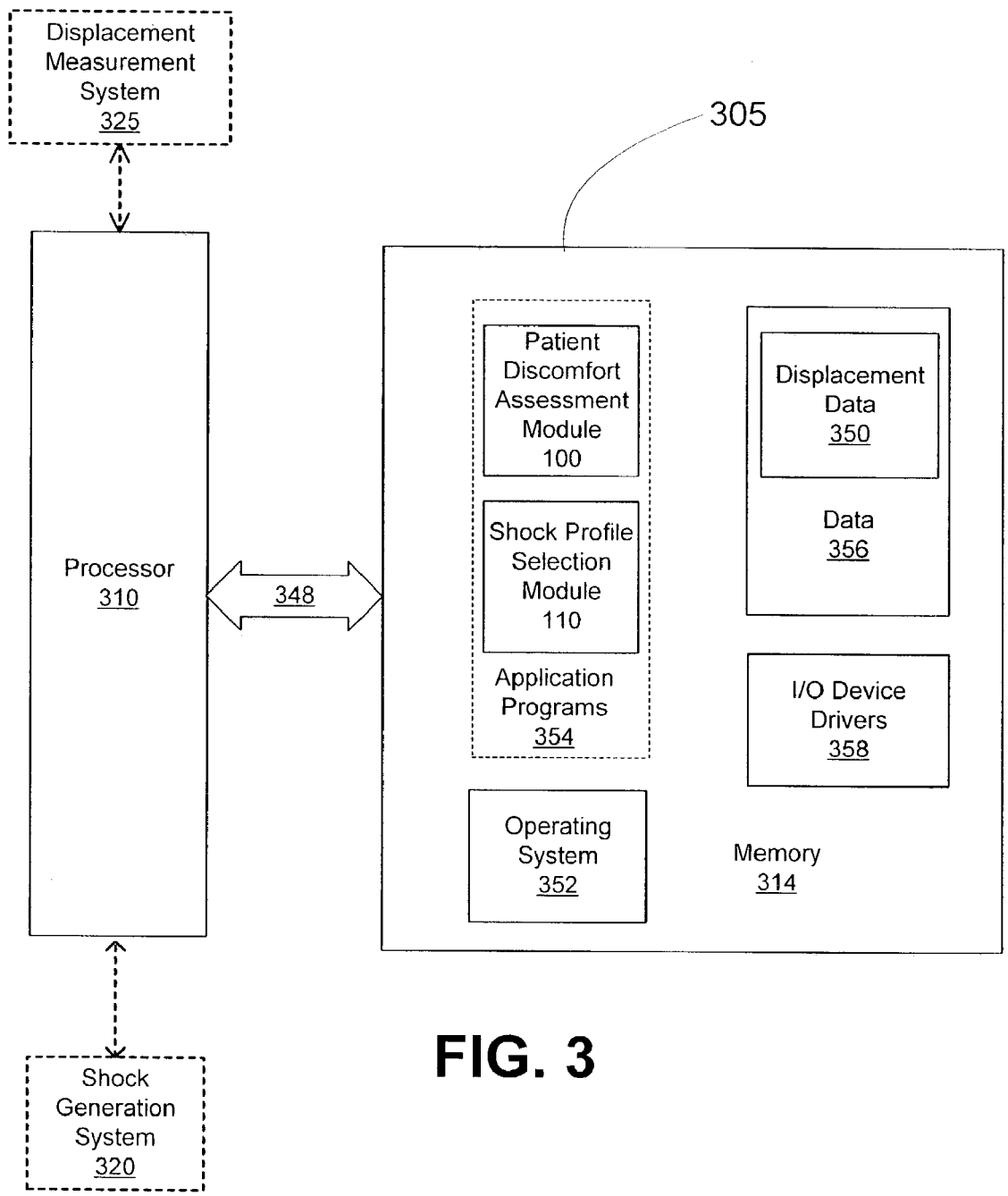
FIG. 3 is a schematic illustration of alternative embodiments of operational circuitry and/or computer program modules suitable for carrying out operations of embodiments of the present invention.

FIG. 2 illustrates one example of an implantable housing 13 containing an electronic circuit 15, which can include one or more amplifiers (not shown) for amplifying sensed cardiac signals. The signals are analyzed by an atrial and/or ventricular fibrillation detector 70 which determines if atrial fibrillation (or other types of cardiac arrhythmias, depending on the specific treatment for which the device is configured) is present. The detector 70 may be one of several known to those skilled in the art. As illustrated, a sensing signal may be provided by the electrode A 50, it will be appreciated by those of skill in the art that the sensing electrode may also be a plurality of sensing electrodes with a plurality of signals, such as bipolar configurations, and may also be electrodes that are positioned in alternate cardiac areas as is known in the art, such as for example, the CS. In this situation, the input line to the detector may be a plurality of lines which if providing only sensing will provide an input to the detector.

In overview, an implantable system for the defibrillation of the atria of a patient's heart comprises: (a) one or more electrodes or electrode pairs configured for delivering a defibrillation pulse, for example, along a desired current pathway(s) in the heart; (b) a pulse generator operatively associated with the atrial defibrillation electrodes for delivering the defibrillation pulse (c) a displacement or discomfort sensor for measuring displacement associated with a delivered shock. The displacement or discomfort sensor may be an accelerometer or other suitable sensor device as will be discussed further herein. Electrodes or electrode pairs may be placed in a variety of different locations. A single electrode may participate in more than one electrode pair, so that, for example, two current pathways are achieved through three defibrillation electrodes. Additional electrodes may be tied together to one member of an electrode pair to provide a single pole, if so desired, and additional electrodes may be provided for following a shock with additional shocks.

Ventricular sensing for timing the shocks for atrial defibrillation may be performed from the RV and/or LV electrodes.

The electronic circuit 15 can also include a cardiac cycle monitor ("synchronization monitor 72") for providing synchronization information to the controller 74. The synchronization can be provided by sensing cardiac activity in the RV, but may also include other sensing electrodes which can be combined with the defibrillation electrodes or employed separately to provide additional assurance that defibrillation shock pulses are not delivered during sensitive portions of the cardiac cycle so as to reduce the possibility of inducing ventricular fibrillation.

The defibrillation electrodes may be configured to sense cardiac cycles from electrical signals from the heart, or may have smaller sensing electrodes placed adjacent thereto and thereby provide input to the electronics package as well as provide a predetermined stimulation shock output to predetermined cardiac areas as directed by the controller. The electronic circuit 15 may also include a pacing system 130 for reading and monitoring cardiac cycles from the electrical signals from the heart sensed by the electrodes.

Still referring to FIG. 2, generally described in operation, upon a signal from the detector 70, the controller 74, in turn, signals the shock generator 79 to generate a shock having a particular selected shock profile. The shock generator 79 may include a capacitor charging circuit 76 which then charges the storage capacitor 78 to a predetermined voltage, typically from a power source such as a battery source (not shown). The storage capacitor is typically 20 to 400 microfarads in size, and may be a single capacitor or a capacitor network (further, as discussed below, separate pulses can be driven by the same or different capacitors). The discharge of the capacitor is controlled by the controller 74 and/or a discharge circuit 80. The controller 74, based on information from the synchronization monitor 72, typically allows or directs the preselected shock profile to be relayed to either a discharge circuit 80 for further processing (i.e., to further shape the waveform signal, time the pulse or pulses, etc.) or directly to an output switch such as switch 82. The controller may also control the desired or proper selection of the predetermined defibrillation electrode pair(s), where multiple defibrillation electrodes are used, to direct the switch 82 to electrically activate a desired electrode pair to align the predetermined electric shock pulse pathway through which the shock pulse is provided. As an alternative to a defibrillation detector, the defibrillation shock profiles may be triggered by an external signal administered by a physician, with the physician monitoring the patient for the appropriate time of administration. The defibrillation shock profiles may be preprogrammed into a library of predetermined shock profiles 120 for selection by the shock profile selection module 110.

The controller 74 includes or is operably associated with a library of selectable predetermined shock profiles 120. The library of selectable predetermined shock profiles 120 includes specifications and/or instructions that define shocks having various shock profiles. The shock profile is selected by the shock profile selection module 110 and communicated to the discharge circuit 80 for use in processing the shock pulse(s) to the desired shock profile specification.

With continued reference to FIG. 2, when a shock is delivered to a patient, the shock related displacement is measured by the shock related displacement measurement module/sensor 125. For example, a displacement sensor 135 may communicate data related to the detected amount of displacement to the displacement measurement module/sensor 125. The displacement sensor 135 may include a one-, two-, or three-dimensional accelerometer. An example of a suitable accelerometer that is commercially available is a Model 2221D from Endevco Corporation, San Juan Capistrano, Calif., U.S.A. The accelerometer may be used to measure peak thoracic acceleration. However, other measurements of shock-induced motion may also be used, for example, scalar velocity and displacement measurements, and integral measurements of scalar acceleration. Furthermore, the measurement of displacement may be made with respect to the thorax or may include displacement measurements of any selected region in the patient. For example, motion of regions of the body other than the thoracic cavity may be used alone, or in combination with, displacement measurements of the thorax. It is currently believed that responses may increase and/or be more globally observable in the body as shock strength or pain increases. Therefore, displacement sensors may be placed on the appendages, the torso, the head or other regions of the subject. The region of the body selected for measurement may include any portion of the patient's body including substantially the entire body.

The displacement is communicated from the shock related displacement measurement module/sensor 125 to the patient discomfort assessment module 100. The patient discomfort assessment module 100 stores information regarding the particular shock profile applied to the patient and the associated displacement. The patient discomfort assessment module 100 compares the shock profiles and the associated displacement to determine which shock profiles are associated with a lesser amount of physical displacement.

It will be appreciated by those of skill in the art that the capacitor 78 may be a single capacitor or a bank of parallel capacitors sufficiently charged and sized to be able to provide at least one shock pulse to predetermined electrodes positioned in the heart. Additionally, the capacitor 78 can be two or more separately charged capacitors (or bank of parallel capacitors) on separate lines to provide two separate and sequential shock pulses as controlled by the controller 74 and/or the discharge circuit 80. However, it is preferred that the capacitor 78 be a relatively large capacitor for insuring sufficient charge and decay period (i.e., long time constant and low tilt) to provide sufficient energy for shock pulses. For example, a capacitor with capacitance in the range of 200–1000 µf or more, having an associated time constant in the range of 30 ms, would typically be charged to approximately 100–200 volts and would deliver a V(peak) in a typical first waveform of about 50–100 volts leading edge. If additional shocks beyond two are administered, then a larger capacitor may be employed. In the alternative wherein the electronic package employs a circuit to further shape the waveform, the capacitor may be charged to a higher voltage range (such as around 200 V).

In one embodiment of the invention, the pulse generator includes a single capacitor 78, and the controller 74 includes a switch (e.g., a crosspoint switch) operatively associated with that capacitor. The controller 74 is configured to provide a shock profile consisting of a biphasic pulse (i.e., a first phase of a pulse of a predetermined polarity followed by a second phase of a pulse of reversed polarity), which consists of a first atrial defibrillation pulse and a biphasic pulse as a second atrial defibrillation pulse. Monophasic and triphasic pulses may also be used.

The controller 74 delivers a preselected electrical pulse to predetermined electrode pairs through a switch 82, which is preferably programmable. The shock generator 79 (including a capacitor charger 76, capacitor 78, and discharge circuit 80), controller 74, and switch 82 thus work in concert to produce and deliver a shock having a particular shock profile. Therefore, it will be appreciated that in operation, in response to an input from the atrial fibrillation detector 70, or a shock profile selection module 110, the controller 74 controls the pulse or shock generator 79 to synchronize the delivery of the timed pulse output to the proper electrode pair in accordance with the cardiac cycle information received from the synchronization monitor 72 and the specific electrode configuration employed by or selected by the device. Further, when employing a biphasic waveform, it will be appreciated by those of skill in the art that the pulse or shock generator 79 can also include a crosspoint switch to switch the polarity of the electrode pair for delivery of the second (inverted or negative) waveform phase. The electronic package may also include a receiver/transmitter coupled to the internal controller 74 for communicating with an external controller. Thus, the pulse regimen could be altered by external input to the controller to alter for example, the waveform, the voltage, the electrode coupling, or even to retrieve data monitoring data received and stored in memory about the number of atrial fibrillation episodes and the effectiveness of the shock level.

In one embodiment of the invention, the switch 82 is programmable (e.g., by remote control such as by a radio signal) to alter the coupling of the pulse generator to the atrial defibrillation electrodes. This feature is advantageously employed when multiple electrodes are implanted so that the electrode pairs that deliver the shocks may be changed to optimize the technique for a particular patient.

The present invention should not be construed as limited to the configuration of FIG. 2, which is intended to encompass any configuration capable of carrying out the operations described herein.

FIG. 3 is a block diagram of exemplary embodiments of data processing systems that illustrates systems, methods, and computer program products in accordance with embodiments of the present invention. The data processing system 305 may be implemented externally or internally with respect to the patient. The shock generation system 320 may be implanted in the patient and the displacement measurement system 325 may include displacement sensors either implanted in the patient along with the shock generation system or situated at internal or external regions of the patient.

The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 3, the memory 314 may include several categories of software and data used in the data processing system 305: the operating system 352; the application programs 354; the input/output (I/O) device drivers 358; a patient discomfort assessment module 100; and the data 356. The data 356 may include displacement data 350 which may be obtained from a displacement measurement system 325. The shock profile selection module 110 may communicate the shock profiles of selected shocks to a shock generation system 320 for delivery to a patient.

As will be appreciated by those of skill in the art, the operating system 352 may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, or proprietary operating systems. The I/O device drivers 358 typically include software routines accessed through the operating system 352 by the application programs 354 to communicate with devices such as I/O data port(s), data storage 356 and certain memory 314 components and/or the shock generation system 320 and displacement measurement system 325. The application programs 354 are illustrative of the programs that implement the various features of the data processing system 305 and preferably include at least one application which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the patient discomfort assessment module 100 and the shock profile selection module 110 being an application program in FIG. 3, as will be appreciated by those of skill in the art, other configurations may also be utilized while still benefiting from the teachings of the present invention. For example, the shock profile selection module 110 may also be incorporated into the operating system 352, the I/O device drivers 358 or other such logical division of the data processing system 305. Thus, the present invention should not be construed as limited to the configuration of FIG. 3, which is intended to encompass any configuration capable of carrying out the operations described herein.

In certain embodiments, the patient discomfort assessment module 100 and shock profile selection module 110 includes computer program code for obtaining data associated with the physical displacement of the body such as the displacement data 350. The displacement data 350 may include data associated with the physical displacement of the body of a subject in response to the administration of a plurality of defibrillation shocks having associated shock profiles. The shock profile selection module 110 may include computer readable code that compares the data associated with the physical displacements for the plurality of shock profiles.

The I/O data port can be used to transfer information between the data processing system 305 and the shock generation system 320 and displacement measurement system 325 or another computer system or a network (e.g., the Internet) or to other devices controlled by the processor. These components may be conventional components such as those used in many conventional data processing systems that may be configured in accordance with the present invention to operate as described herein.

Figure 4:
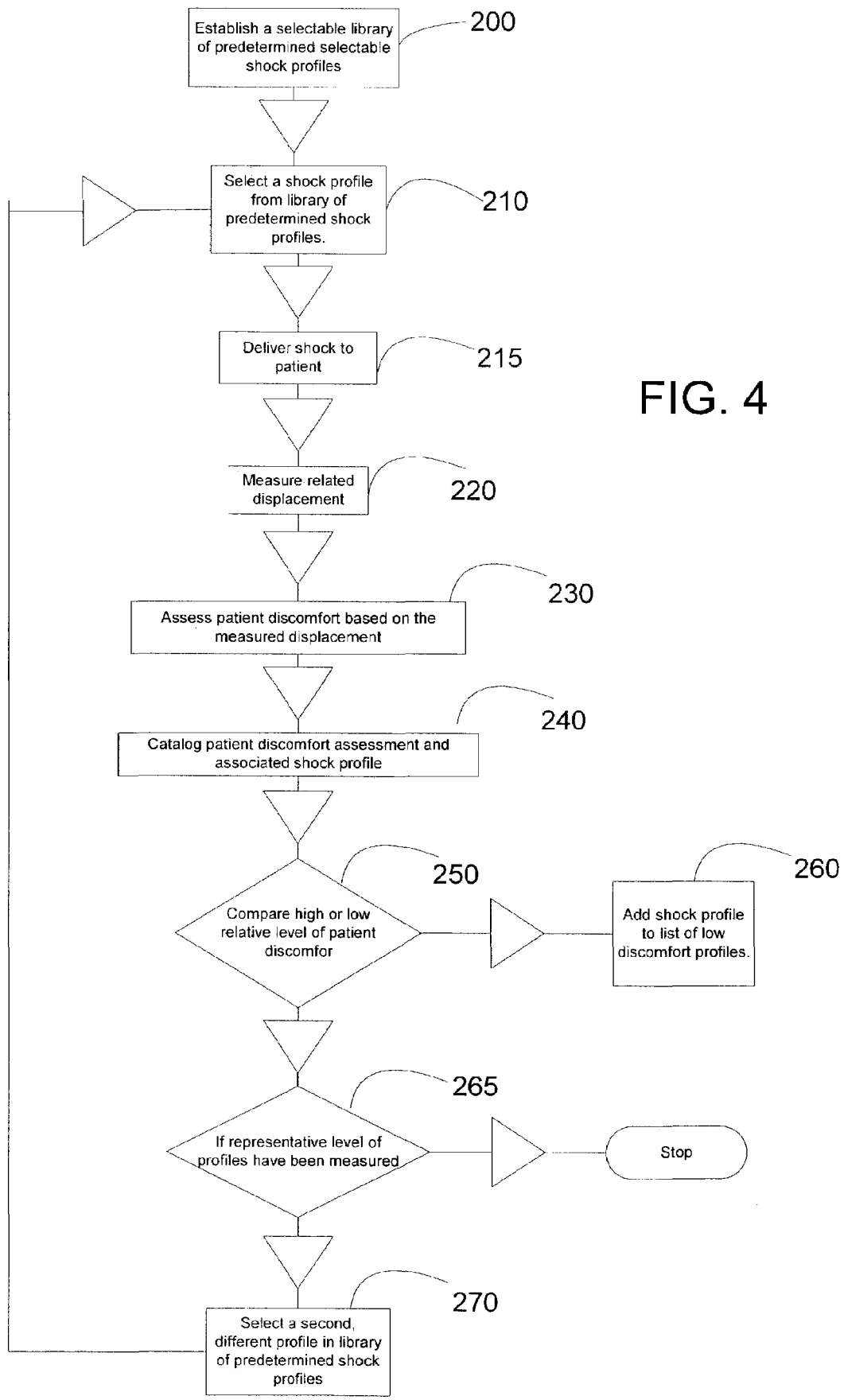
FIG. 4 is a flowchart illustrating operations that can be carried out according to embodiments of the present invention.

Referring now to FIG. 4, exemplary operations are shown. The exemplary operations depicted in FIG. 4 may be carried out by the system depicted in FIG. 2 or other suitable atrial defibrillation systems. The library of predetermined shock profiles 120 includes shock profiles that may be associated with an unknown displacement or amount of discomfort for a particular patient (at the time of implantation). For each shock profile in the library of predetermined shock profiles 120 (Block 200), the shock profile selection module 110 selects a shock profile from the library of predetermined shock profiles 120 that may have an unknown associated discomfort level (Block 210). 30 The shock profiles 120 may also be selected based on a prior determination that the shock profiles 120 are likely to have a relatively low level of associated discomfort. For example, the shock profiles 120 may be selected based on prior testing of a general population. The shock profile is communicated from the controller 74 to the discharge circuit 80. A shock is delivered to the patient according the selected shock profile by the discharge circuit 80 and the capacitor charger 76 (Block 215). The displacement associated with the shock is detected by a displacement sensor 135 and communicated to the shock related displacement measurement module/sensor 125 (Block 220).

The shock related displacement measurement module/sensor controller 125 communicates the shock related displacement measurement to the patient discomfort assessment module 100, which records and analyzes the displacement associated with the selected shock profile (Block 230). It may be appreciated that a patient's discomfort level may be difficult to measure directly or in absolute terms, and therefore, analysis of the displacement and assessment of patient discomfort may involve estimating the patient discomfort on a relative scale. The assessment of patient discomfort may involve an assumption that a simple linear correlation exists between the displacement value and patient discomfort. The assessment could also involve a nonlinear scale. For example, above a certain threshold, a small difference in displacement may correspond to a larger increase in patient discomfort than the same difference at a lower displacement value. If more than one displacement value is recorded, the assessment could also involve weighting various displacement values. For example, movement in the appendages may be weighted more heavily than movement in the thoracic cavity when assessing patient discomfort based on displacement. Various other statistical algorithms to correlate displacement and discomfort may also be used.

The patient discomfort assessment and related shock profile can be cataloged in the shock profile selection module 110 (Block 240). The patient discomfort assessment is compared (Block 250). If the patient discomfort is low, e.g., if the patient discomfort is below a predetermined amount, then the shock profile is added to a list of low discomfort profiles (Block 260) and stored in the shock profile selection module. If a representative number of profiles have been measured, the administration of shocks and assessment of associated pain is stopped (Block 265). The next profile in the library of predetermined shock profiles is selected (Block 270). The steps in FIG. 4 (Blocks 200, 210, 220, 230, 240, 250, and 260) are then repeated for each shock profile. Therefore, a list of relatively low discomfort profiles is created.

The operations shown in FIG. 4 may be modified, for example, to select a single shock profile having the lowest relative measured displacement. The list of relatively low discomfort shock profiles may be used in various ways. For example, the shock profile selection module may be programmed to only select the shock profile having the lowest relative measured displacement if future defibrillating shocks are delivered to the patient. Alternatively, the shock profile selection module may be programmed to alternate the selection of shock profiles that are below a predetermined displacement value for future defibrillating shocks delivered to a patient.

The first and second shock profiles may be configured for treating any form of cardiac tachyarrhythmias. In particular, the shock profiles may be configured to treat atrial fibrillation, flutter, or hemodynamically stable ventricular tachyardia. Each shock profile may include a shock vector and waveform profile. Each shock profile may vary in at least one of the shock vector and the shock pulse waveform. The delivery of the shock at (Block 215) and the measurement of related displacement at (Block 220) may be performed after administering anestetic to the patient or while the patient is asleep. The measurement of related displacement at (Block 220) may be determined from an accelerometer, for example, a three dimensional accelerometer. The sensor or accelerometer may be implanted in the patient, for example, mounted in the implantable housing, or positioned externally on the patient or subcutaneously or percutaneously. The measuring and delivering steps (Blocks 215 and 220) may be carried out in vivo while the defibrillator is implanted in the patient. The measuring and delivering steps (Blocks 215 and 220) may be performed over a plurality of different patients selected to provide a statistically relevant predictive population. The steps depicted in FIG. 4 may also be used to generate set-up operational parameters at initial implantation. In addition or alternatively, the measuring and delivering steps (Blocks 215 and 220) may be performed individually on each patient to establish a customized shock profile for each respective patient to thereby reduce a patient's discomfort to administered defibrillating shocks. It is possible that the pain associated with a particular shock profile may change for an individual patient over time. Therefore, the steps depicted in FIG. 4 may be repeated periodically to reevaluate the shock profiles, for example, while the patient is asleep.

Figure 5:
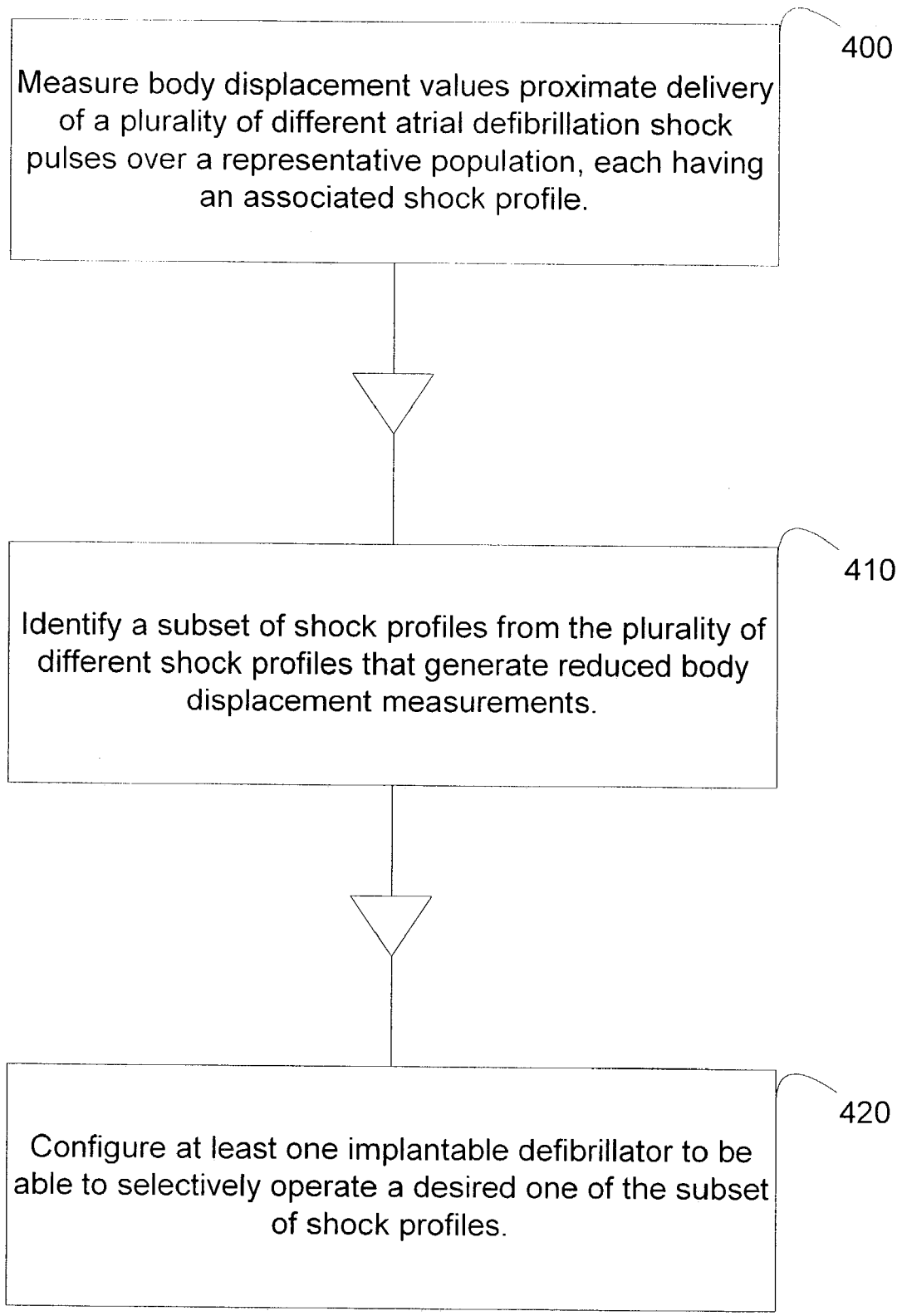
FIG. 5 is a flowchart illustrating operations according to further embodiments of the present invention.

An example of operations of embodiments of the present invention is depicted in FIG. 5. The displacement values can be measured or obtained proximate the delivery of a plurality of different atrial defibrillation shock pulses (Block 400). As used herein, when a displacement measurement is made "proximate" a shock, the measurement is made during or after the shock such that the displacement can be correlated with the shock treatment. Each shock pulse has an associate shock profile, and the measurements are taken over a plurality of different patients selected to provide a statistically relevant predictive population. The system identifies a subset from the plurality of different shock profiles that generate a relatively reduced body displacement measurement over the representative population (Block 410), for example, by selecting a shock profile having a lesser amount of measured physical displacement based on a statistically determined lesser amount of measured physical displacement over the population. Implantable defibrillators can be configured or preprogrammed to be able to selectively operate a desired one of the subset of shock profiles or programmed after implantation to do so. (Block 420).

The representative or predictive population may be segmented by physiological and/or epidemiological factors such as race, gender, age, diet, exercise habits, socio-economic background, and selected measurements of health (i.e., diabetes, blood pressure, cholesterol levels and the like). The selected shock profile may be based on the optimum shock profile having the lowest pain/discomfort as measured over the relevant population segment for a particular patient's characteristics. For example, implanted defibrillators may be further programmed to select a particular subset of shock profiles for administration to a particular patient based on the observation of low physical displacement in a corresponding statistically relevant predictive population, and/or measurement based on individualized physical displacement of the patient in response to one or more of the subset of shock profiles. The shock profiles in the subset may be further studied with respect to the individual patient, for example, using the steps depicted in FIG. 4 to determine which shock profile causes the least discomfort for the individual.

In certain embodiments, measurements of body displacement values proximate the delivery of a plurality of different atrial defibrillation shock pulse may be taken in an animal population to identify a subset of shock profiles that generate reduced body displacement measurements. Implantable defibrillators may then be configured to be able to selectively operate a desired one of the subset of shock profiles in a human or in another animal. Testing body displacement in animals may reduce the need to test defibrillation shocks in human subjects.

Figure 6A:
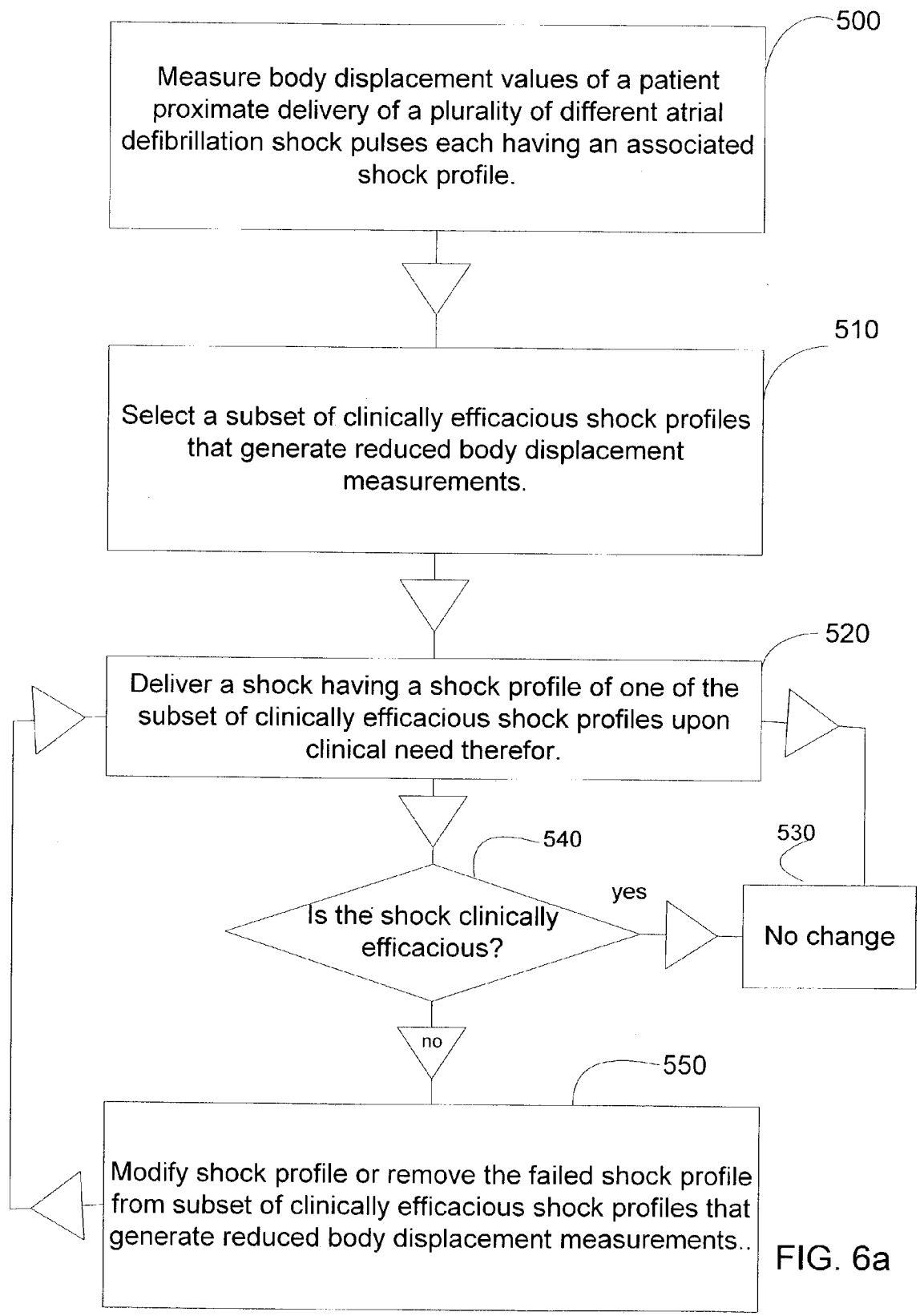
FIG. 6a is a flowchart illustrating operations according to still further embodiments of the present invention.

An example of an embodiment according to the present invention is depicted in FIG. 6a. Generally stated, a shock profile is clinically efficacious if it halts the atrial fibrillation and the cardiac rhythm is returned to normal sinus rhythm. Therefore, a shock profile that is not clinically efficacious is preferably discarded even if it causes a minimal level of physical displacement. Furthermore, it is possible that clinical efficacy may change over time for a particular patient. Therefore, it is desirable to monitor the clinical efficacy of shock profiles and modify the shock profiles if the shock profile is no longer efficacious.

As shown in FIG. 6a, a system according to the invention can measure body displacement values of the reaction of a patient to the delivery of a plurality of different atrial defibrillation shock pulses, each having an associated shock profile (Block 500). The system selects a subset of clinically efficacious shock profiles that generate reduced body displacement measurements (Block 510). The operations depicted in Blocks 500 and 510 may be carried out, for example, using the steps illustrated in FIGS. 4 or 5.

The system delivers a shock having a shock profile of one of the subset of shocks that have been previously determined to be clinically efficacious (Block 520). The system determines if the delivered shock is clinically efficacious (Block 540). If the shock is clinically efficacious, the system can direct the shock profile selection to remain the same and makes no change to the shock selection (Block 530) and additional shocks may be delivered (Block 520). If the shock is not clinically efficacious, the shock profile is either modified or removed from the subset of clinically efficacious shock profiles that generate reduced body displacement measurements (Block 550). Modifications to the shock profile may include, for example, increasing voltage or strength of the shock, adding additional pulses to the shock profile, modifying the waveform, or changing any other shock profile characteristic to increase the likelihood of obtaining clinical efficacy.

Anatomically, the heart includes a fibrous skeleton, valves, the trunks of the aorta, the pulmonary artery, and the muscle masses of the cardiac chambers (ie., right and left atria and right and left ventricles). The schematically illustrated portions of the heart 30 illustrated in FIG. 6b includes the right ventricle "RV" 32, the left ventricle "LV" 34, the right atrium "RA" 36, the left atrium "LA" 38, the superior vena cava 48, the coronary sinus "CS" 42, the great cardiac vein 44, the left pulmonary artery 45, and the coronary sinus ostium or "os" 40.

The driving force for the flow of blood in the heart comes from the active contraction of the cardiac muscle. This contraction can be detected as an electrical signal. The cardiac contraction is triggered by electrical impulses traveling in a wave propagation pattern which begins at the cells of the SA node and the surrounding atrial myocardial fibers, and then traveling into the atria and subsequently passing through the AV node and, after a slight delay, into the ventricles.

The beginning of a cardiac cycle is initiated by a P wave, which is normally a small positive wave in the body surface electrocardiogram. The P wave induces depolarization of the atria of the heart. The P wave is followed by a cardiac cycle portion which is substantially constant with a time constant on the order of 120 milliseconds ("ms").

The "QRS complex" of the cardiac cycle occurs after the substantially constant portion. The dominating feature of the QRS complex is the R wave which is a rapid positive or negative deflection. The R wave generally has an amplitude greater than any other wave of the cardiac cycle, and has a spiked shape of relatively short duration with a sharp rise, a peak amplitude, and a sharp decline. The R wave is the depolarization of the ventricles and therefore, as used herein, the term "ventricle activations" denotes R waves of the cardiac cycle. The QRS complex is completed by the S wave, which is typically a small deflection that returns the cardiac signal to baseline.

Following the S wave, the T wave occurs after a delay of about 250 ms. The T wave is relatively long in duration (e.g., about 150 ms). The cardiac cycle between the S wave and the T wave is commonly referred to as the ST segment. The T wave is a sensitive part of the cardiac cycle, during which an atrial defibrillation shock is to be avoided, in order to reduce the possibility of induced (and often fatal) ventricular fibrillation. The next cardiac cycle begins with the next P wave. The typical duration of a complete cardiac cycle is on the order of about 800 ms.

Various embodiments of the present invention can be illustrated with reference to FIG. 6b. The defibrillator 10 of FIG. 6b includes an implantable housing 13 that contains a hermetically sealed electronic circuit 15 (see FIG. 2). The housing can include an electrode comprising an active external portion 16 of the housing, with the housing 13 preferably implanted in the left thoracic region of the patient (e.g., subcutaneously, in the left pectoral region) in accordance with known techniques as described in G. Bardy, U.S. Pat. No. 5,292,338. The system includes a first catheter 20 and a second catheter 21, both of which are insertable into the heart (typically through the superior or inferior vena cava) without the need for surgical incision into the heart. The term "catheter" as used herein includes "stylet" and is also used interchangeably with the term "lead". Each of the catheters 20, 21 contains electrode leads wires 20a, 20b, 20c, 21d, 21e, and 21f, respectively, with the small case letter designation corresponding to the large-case letter designation for the defibrillation electrode to which each lead wire is electrically connected.

Figure 6B:
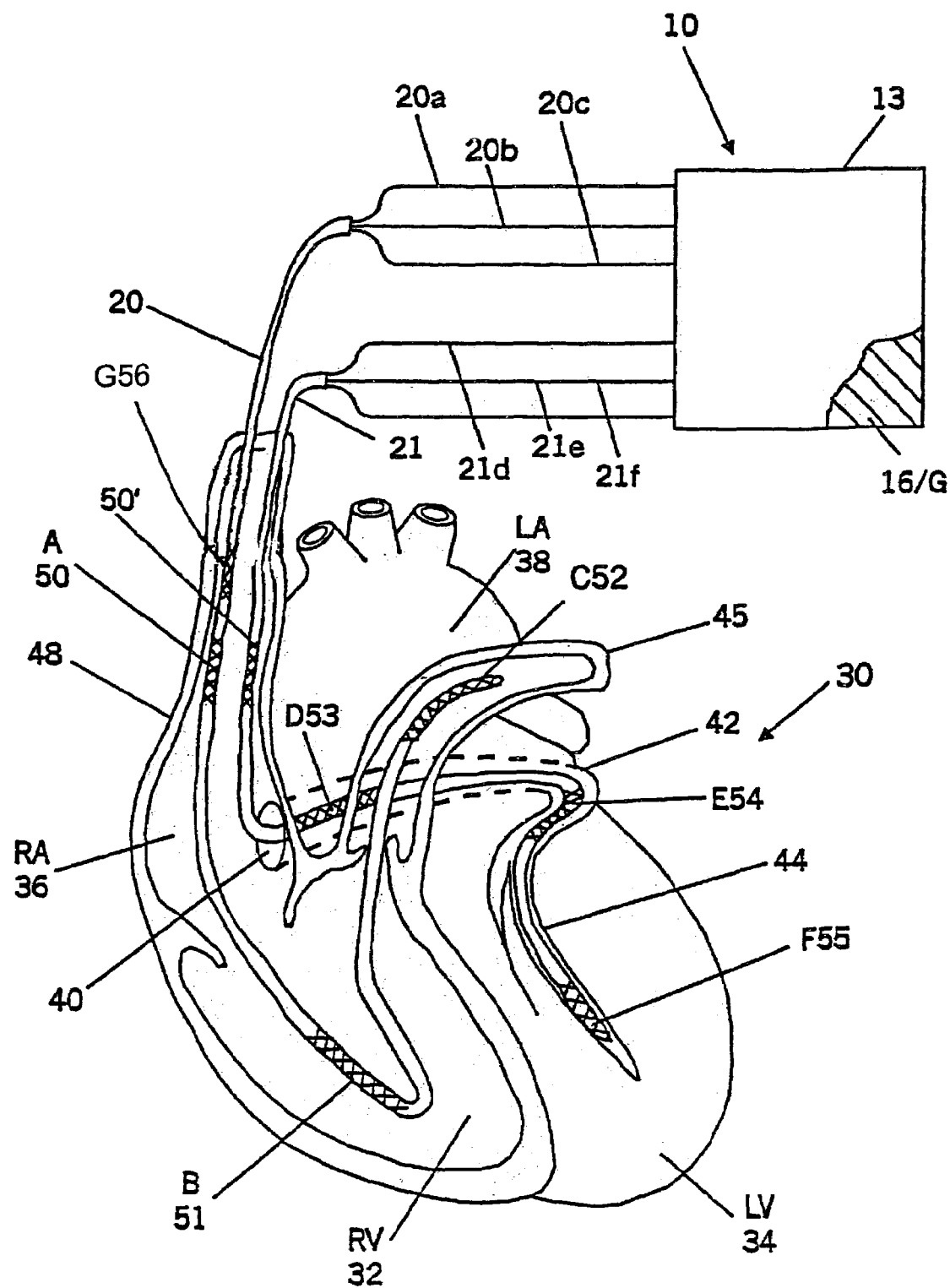
FIG. 6b is a schematic illustration of an implantable apparatus with exemplary electrode placements according to embodiments of the present invention.

As illustrated in FIG. 6b, the catheter 20 includes an electrode A; 50 that resides in the right atrium (the term "right atrium" herein including the superior vena cava and innominate vein), an electrode B; 51 positioned in the right ventricle (preferably in the right ventricular apex), and an electrode C; 52 positioned within the left pulmonary artery (the term "left pulmonary artery" herein includes the main pulmonary artery and the right ventricular outflow tract).

The second catheter lead 21 includes, from proximal to distal, a first electrode D; 53 positioned in the proximal coronary sinus, adjacent the coronary sinus ostium or "os" 40; a second electrode E; 55 positioned in the distal coronary sinus (preferably as far distal in the coronary sinus as possible) (the term "distal coronary sinus" herein includes the great cardiac vein); and a third electrode F; 56 at or adjacent the tip of the catheter in a coronary vein on the surface (preferably the posterolateral surface) of the left ventricle (e.g., in the lateral-apical left ventricular free wall). The position of electrode F may be achieved by first engaging the coronary sinus with a guiding catheter through which a conventional guidewire is passed. The tip of the torqueable guidewire is advanced under fluoroscopic guidance to the desired location. The lead 21 on which electrode F is mounted passes over the guidewire to the proper location.

The guidewire is withdrawn and electrode F is incorporated into the defibrillation lead system.

Electrode A, 52 may optionally be positioned on lead 21 and retain the same operable positions described above as when positioned on lead 20.

The active external portion of the housing 16 serves as an optional seventh electrode G, which may be used for either atrial or ventricular defibrillation.

The electrodes described in FIG. 6b and the specification above may, for convenience, be designated by the most adjacent structure. These structures are: the right atrium (RA), right ventricle (RV), pulmonary artery (PA), coronary sinus ostium (OS), distal coronary sinus (CS), and left ventricle (LV). Thus, when applied to electrodes the electrodes of FIG. 6b:

RA means electrode A, 50;
RV means electrode B, 51;
PA means electrode C, 52;
OS means electrode D, 53;
CS means electrode E, 54; and
LV means electrode F, 55.

Numerous configurations of capacitor and control circuitry may be employed. The power supply may include a single capacitor, and the control circuit may be configured so that both the auxiliary pulse and the defibrillation pulse are generated by the discharge of the single capacitor. The power supply may include a first and second capacitor, with the control circuit configured so that the auxiliary pulse is generated by the discharge of the first capacitor and the defibrillation pulse is generated by the discharge of the second capacitor. In still another embodiment, the power supply includes a first and second capacitor, and the control circuit may be configured so that the auxiliary pulse is generated by the discharge (simultaneous or sequential) of both the first and second capacitors, and the defibrillation pulse likewise generated by the discharge of the first and second capacitors.

Table 1 below illustrates examples of numerous different combinations of electrodes that may be employed to carry out the atrial defibrillation. In Table 1, the polarity of electrode is illustrated by the direction of the arrows, but polarity is not critical and can be reversed. The ventricular defibrillation electrodes are noted because the implantable device can be configured to selectively deliver both ventricular and atrial defibrillation pulses at the appropriate times. As will be seen from Table 1, a combination atrial and ventricular defibrillator may employ some or all of the electrodes illustrated in FIG. 6b, and numerous combinations thereof. The electrodes may be configured on one lead and/or intraluminal catheters or a plurality of leads and/or catheters.

TABLE 1

Electrode configurations.

| | Ventricular Defibrillation | Atrial Defibrillation |
|---|---|---|
| 1 | RA -> RV | RA -> CS |
| 2 | RA -> RV | PA -> OS |
| 3 | RA -> RV | RA -> OS |
| 4 | RA -> RV | OS -> CS |
| 5 | RA -> RV | CS -> PA |
| 6* | RA -> RV | PA -> RA |
| 7 | PA -> LV | RA -> CS |
| 8 | PA -> LV | PA -> OS |
| 9 | PA -> LV | RA -> OS |
| 10 | PA -> LV | OS -> CS |

TABLE 1-continued

Electrode configurations.

| | Ventricular Defibrillation | Atrial Defibrillation |
|---|---|---|
| 11 | PA -> LV | CS -> PA |
| 12 | PA -> LV | PA -> RA |
| 13 | RA -> LV | RA -> CS |
| 14 | RA -> LV | PA -> OS |
| 15 | RA -> LV | RA -> OS |
| 16 | RA -> LV | OS -> CS |
| 17 | RA -> LV | CS -> PA |
| 18 | RA -> LV | PA -> RA |
| 19 | PA -> RV | RA -> CS |
| 20 | PA -> RV | PA -> OS |
| 21 | PA -> RV | RA -> OS |
| 22 | PA -> RV | OS -> CS |
| 23 | PA -> RV | CS -> PA |
| 24* | PA -> RV | PA -> RA |
| 25 | RV -> LV | RA -> CS |
| 26 | RV -> LV | PA -> OS |
| 27 | RV -> LV | RA -> CS |
| 28 | RV -> LV | OS -> CS |
| 29 | RV -> LV | CS -> PA |
| 30 | RV -> LV | PA -> RA |

Those skilled in the art will appreciate that still additional electrode combinations are possible for both atrial and ventricular defibrillation by employing the "active can" electrode G, 16, as discussed herein. In addition, multiple electrodes can be electrically coupled or "tied" together to form a single pole. For example, a shock can be delivered from either the RV or LV as one pole to the PA and OS tied together as the other pole.

Any suitable waveform may be used to carry out the present invention, including both monophasic, biphasic and triphasic waveforms. Various amplitudes, polarities, and durations of waveforms may be studied, as will be apparent to those skilled in the art.

Figure 7:
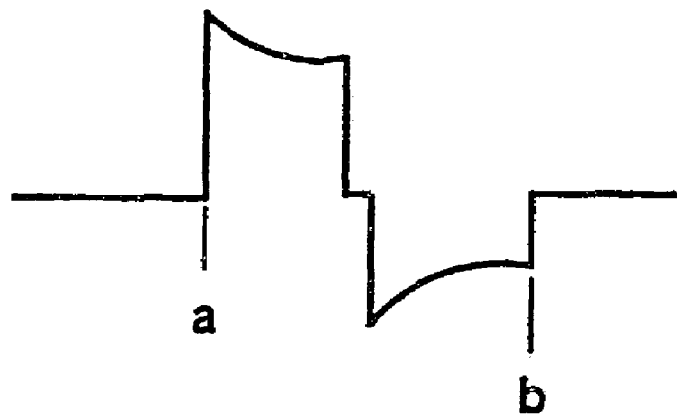
FIG. 7 illustrates a biphasic waveform that may be used to carry out atrial or ventricular defibrillation in accordance with embodiments of the present invention.

For example, FIG. 7 illustrates a biphasic reverse exponential waveform that may be used to carry out atrial or ventricular defibrillation in accordance with the present invention, with the waveform being between time a and time b.

Figure 8:
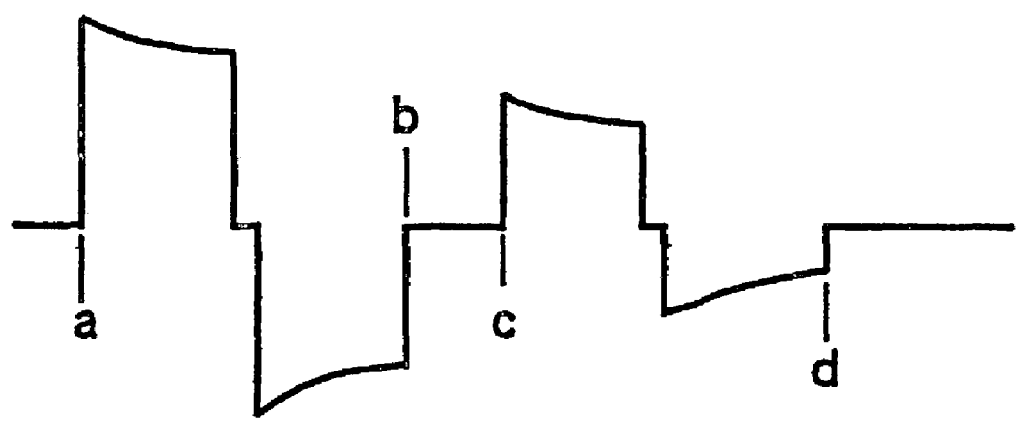
FIG. 8 illustrates first and second biphasic waveforms that may be used to carry out atrial or ventricular defibrillation along two current pathways in accordance with embodiments of the present invention.

When dual current pathways are employed for the defibrillation shock, the waveform for each current pathway may be monophasic or biphasic. For example, FIG. 8 illustrates first and second reverse exponential biphasic waveforms that may be used to carry out atrial or ventricular defibrillation along two current pathways in accordance with the present invention. The first waveform of FIG. 8 is represented between time a and time b; the second waveform of FIG. 8 is represented between time c and time d. The time between the first and second waveforms (the time from time b to time c), will be apparent to those skilled in the art, but is preferably from 0 to 100 or 500 milliseconds, and more preferably from 0.1 to 50 milliseconds.

Figure 9:
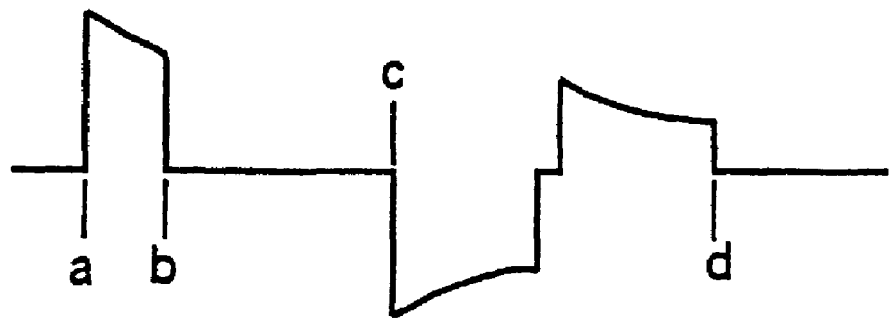
FIG. 9 illustrates a first auxiliary waveform and a second biphasic waveform that may be used to carry out atrial or ventricular defibrillation along two current pathways in accordance with embodiments of the present invention.

FIG. 9 illustrates a first auxiliary waveform (from time a to time b) and a second reverse exponential biphasic waveform (from time c to time d) that may be used to carry out atrial or ventricular defibrillation along two current pathways in accordance with the present invention.

Additional shock profiles may be used having various properties including waveform, polarity, shape, periodicity, energy, voltage, etc. Exemplary shock profiles are described in U.S. Pat. No. 6,327,500 to Cooper et al., U.S. Pat. No. 5,978,705 to KenKnight et al. U.S. patent application Ser.

No. 10/012,115 filed Nov. 13, 2001, the contents of which are hereby incorporated by reference as if recited in full herein.

EXAMPLE

The invention will now be described with reference to the following Examples, which are to be non-limiting to the claimed invention.

Six adult Yorkshire pigs (32±4 kg) were investigated using methods, systems, and apparatuses according to the present invention.

Animal Preparation

As a preanesthetic agent, 2 mg/kg telazol was given intramuscularly. About 10 minutes later, pentothal (2–6 mg/kg) was administered intravenously. Next, the animal was laid dorsally along the midline of a V-cross-section fluoroscopy table, intubated, and placed on a volume-cycled ventilator (tidal volume: 15–20 ml/kg; respiratory rate: 8–12 breaths/min) with a 2–3% isoflurane/oxygen mixture. During the experiment, lactated Ringer's solution was infused intravenously, and the isoflurane concentration was maintained at 1–3% to maintain a deep plane of anesthesia. Every 30–60 minutes, blood gas and chemistry analyses were conducted. Based on these analyses, the ventilator settings were adjusted and supplemental electrolytes added to the Ringer's solution as necessary to maintain the blood gases within normal ranges.

An 8F sheath was placed in the left femoral artery percutaneously for continuous arterial pressure monitoring. The animal was instrumented for continuous lead II ECG and esophageal temperature monitoring. A heated water blanket was used to maintain body temperature at approximately 37° C. To achieve complete neuromuscular blockade during the last treatment of the investigation, a 4 mg/kg intravenous bolus of succinylcholine chloride was administered, followed by an intravenous drip of 24 mg/min for maintenance. After the completion of the experimental protocol, euthanasia was induced with an intravenous bolus of potassium chloride.

As part of the test treatments, the thorax was opened and reapproximated. The initial chest opening was accomplished via a median sternotomy. The skin and subcutaneous tissue were incised with a scalpel over the midline of the sternum. The pectoral musculature was incised and elevated from the sternebrae with electrocautery. The sternum was then cut along its midline with an oscillating saw. Before reapproximation, a thoracostomy tube was placed subcostally and lateral to the midline. The sternotomy was then closed. First, approximation of the ribs was performed with preplaced suture umbilical tape; next, the pectoralis muscles, subcutaneous tissues, and skin were closed in separate layers. After thoracic reapproximation, a suction pressure of approximately −20 cm $H_2O$ was maintained with an underwater thoracic seal drainage system (commercially available under the tradename PLEUR-EVAC™ from Deknatel, Inc., Fall River, Mass., U.S.A.).

The left and right phrenic nerves were severed as part of one of the experimental treatments. Following median sternotomy and retraction of the thoracic cavity, the heart was lifted sequentially to the left and right, exposing the right and left phrenic nerves; these nerves were severed with scissors at their insertion into the diaphragm after careful dissection.

Instrumentation

All defibrillation catheters were positioned transvenously under fluoroscopic guidance. Through a jugular vein, a defibrillation lead (PERIMETER™#7109, Guidant Corp., St. Paul, Minn., U.S.A.) with a distal 6-cm electrode was situated in the CS. Care was taken to not place this lead in the persistent superior vena cava, which is present in this species. Through another jugular vein, a second defibrillation lead (Endotak DSP, Guidant Corp, St. Paul, Minn., U.S.A) was situated with its tip in the apex of the RV; along this lead, coil electrodes of 4.5 cm and 6.0 cm resided in the RV and the superior ventricular cavity (SVC), respectively. The SVC electrode 56 was positioned so that its distal end lay at the junction between the SVC and RA. Lastly, a defibrillator can housing (Can) was situated subcutaneously in the left pectoral thorax.

With the animals situated dorsally along the midline of the V-shaped fluoroscopy table, a 3-dimensional accelerometer (Model #3D-DIN; Vernier Corp., Beaverton, Oreg., U.S.A.) was sutured over the sternum. This accelerometer of approximately 1″ cube and mass of <2 oz. outputs three independent analog signals between 0 and 5 V (corresponding to accelerations of −50 to 50 $m/s^2$) representing the accelerations experienced along each of the three axes along a standard Cartisian coordinate system. For each test shock, these accelerations were recorded at 6 kHz for a total of 4 seconds, commencing approximately 1 s prior to the shock, and communicated to a laptop microcomputer (PENTIUM™ PC, Gateway, Inc., Appleton, Wis.) running standard data acquisition software (WINDAQ™, Dataq Instruments, Akron, Ohio, U.S.A.), where they were later transferred for off-line analyses. The animals' legs were lightly restrained individually, with rope, primarily so that their front hoofs wouldn't bump the accelerometer upon rebound of their shock-induced motion. For the last three animals, along with the thoracic accelerations, a scaled version of the defibrillation shock voltage was recorded using the data acquisition system.

Test defibrillation shocks were delivered by a VENTAK™ Endocardio Defibrillator (ECD) #2815, Guidant Corp, St. Paul, Minn., U.S.A., which output a biphasic fixed tilt (60% first-phase tilt/40% second-phase tilt) 140 µF capacitance discharge. The device was modified to deliver shocks of pre-set peak voltage, and upon the delivery of each shock, the displayed shock parameters that were documented included the delivered energy and the shock resistance. To minimize the likelihood of induction of ventricular tachyarrhythmias, shocks were synchronized by the VENTAK™ ECD to intrinsic ventricular activations from an integrated bipole electrogram from the tip of the RV defibrillation lead ($RV_{tip} \rightarrow RV_{coil}$). All shocks were delivered in normal sinus rhythm post-expiration and pre-inspiration.

Experimental Protocol

Figure 10:
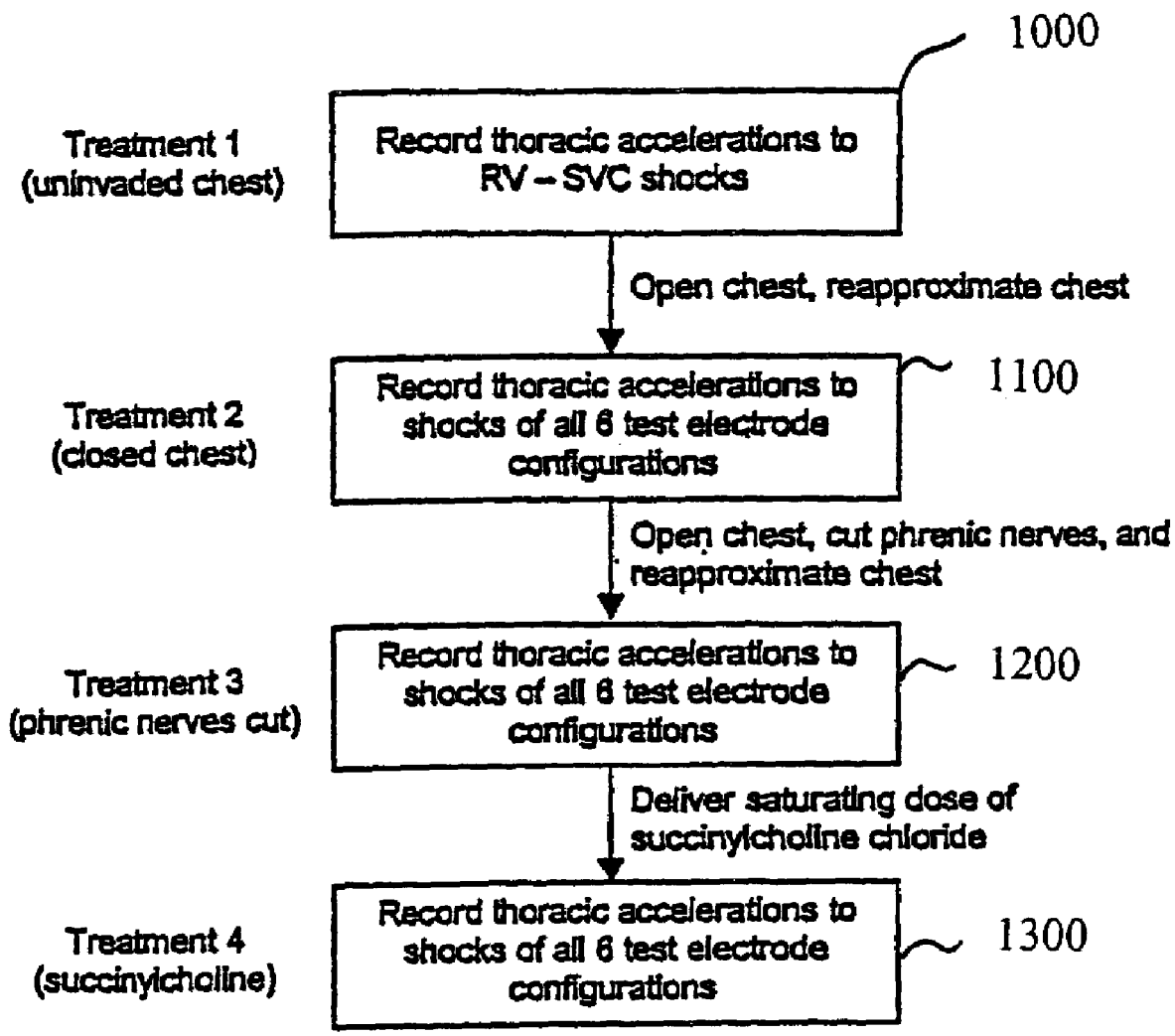
FIG. 10 is a flowchart illustrating operations according to embodiments of the present invention.
Figure 11:
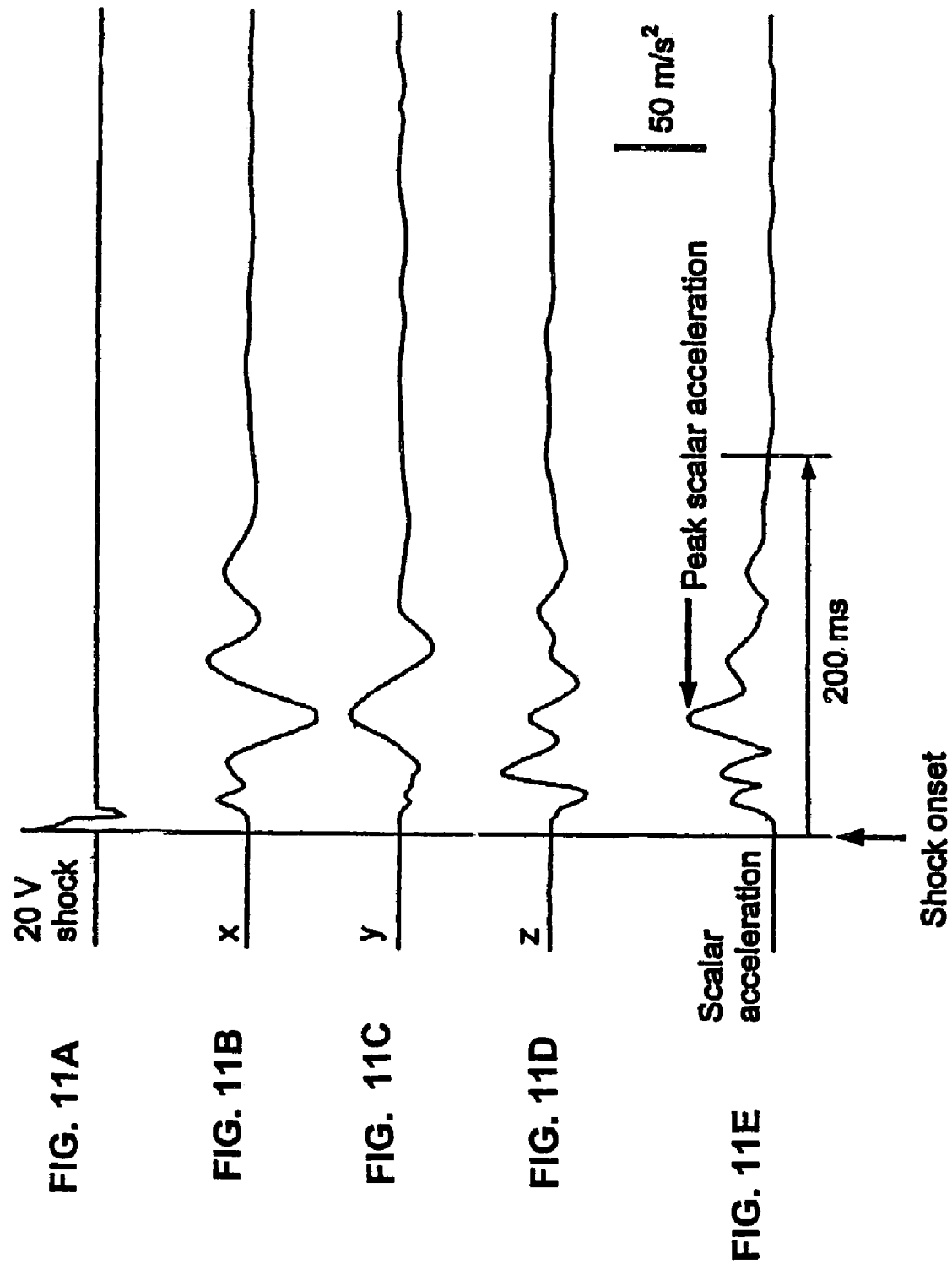
FIGS. 11A–E are a graphs illustrating an exemplary shock and the associated displacement over time in the x, y, z directions and scalar acceleration.

The thoracic accelerations to six test electrode configurations were investigated: RV→Can, RV→SVC, CS→Can, RV→CS, SVC→Can, and CS→SVC according to FIG. 10. The test configurations described herein are referred to as "cathode" →"anode" for the initial phase of the defibrillation waveform. All four of the defibrillation electrodes remained present during the entire experimental protocol, so that electrodes not utilized by particular test configurations were electrically passive during the delivery of these shocks. Shocks of seven pre-set peak voltages of 15V, 20V, 30V, 50V, 100V, 300V, and 600 V were tested in each electrode configuration. Each of the shocks of pre-set peak voltages 15V, 20V, 30V, 50V, 100V, 300V, and 600 V conformed to the waveform of the 20V waveforem depicted in FIG. 11A. As would be understood by those of ordinary skill in the art, other waveforms of various tilt or duration may be used, including monophasic, biphasic, and triphasic waveforms Once the leads were situated and the accelerometer and associated instrumentation in place, the experimental protocol was begun. The experimental protocol was comprised of four sequential treatments, referred to herein as treatments 1–4 (FIG. 10). In treatment 1, with the thorax still uninvaded, the responses to shocks of the seven different magnitudes in the RV→SVC electrode configuration were delivered (Block 1000). In treatment 2, after opening and reapproximating the thorax, the responses to shocks of the seven amplitudes in each of the six test configurations were recorded (Block 1100). In treatment 3, the chest was re-opened, the phrenic nerves were cut, the chest was reapproximated, and the same set of measurements (seven different peak voltages over six different test electrode configurations as described above for FIGS. 10) were performed (Block 1200). In treatment 4, another set of test shocks were delivered (seven different peak voltages over six different test electrode configurations as described above for FIGS. 10), this time approximately 15 minutes after the delivery of a bolus and maintenance administration of succinylcholine chloride (Block 1300). In treatments 2–4 (Blocks 1100, 1200, and 1300), the order of the configurations to be tested within each treatment was initially randomized, followed by the sub-randomization of the order of delivery of the seven shock amplitudes within each configuration. In treatment 1 (Block 1000), the order of the seven RV→SVC shock amplitudes was also randomized.

In addition to treatments 1–4, the response to an extra 100 $V_{peak}$RV→SVC shock was recorded after each set of 7 shocks in each treatment/electrode configuration set. A total of 152 shocks were given.

Data processing

Off-line, the thoracic accelerations undergone by each animal due to each test shock were analyzed. Referring to FIGS. 11A–E, an example of a 20V shock (FIG. 11A) and the resulting displacement, x axis acceleration (FIG. 11B), y axis acceleration (FIG. 11C), z axis acceleration (FIG. 11D), scalar acceleration (FIG. 11E) and peak scalar acceleration 2500 are shown.

The x, y, and z accelerations (FIGS. 11B–D) were analyzed as follows. First, the x, y, and z accelerations (FIGS. 11B–D) due to each shock were scanned anterograde and a rough time of motion onset was identified as the time at which the first of any of the x, y, and z axis accelerations (FIGS. 11B–D) initially underwent a change in acceleration of >1.5 m/s² from the mean acceleration of the initial 0.5 s of recording. Next, the x, y, and z axis accelerations (FIGS. 11B–D) were independently "zeroed" by subtracting from each signal the mean of each signal between 50 and 100 ms prior to the previously identified rough time of motion onset. Next, the (more precise and accurate) time of motion onset was identified for the accelerations as the initial time at which the first of any of the three accelerations underwent an acceleration greater than a value equal to six times the standard deviation of each acceleration between 50 and 100 ms prior to the previously defined rough time of motion onset. Next, the scalar acceleration (FIG. 11E) was computed as the square root of the sum of the square of the three zeroed accelerations corresponding to x, y, and z axis accelerations (FIGS. 11B–D) computed time point by time point. Lastly, the peak scalar acceleration 2500 due to each test shock was defined as the maximum scalar acceleration experienced in the 200 ms after the time of motion onset.

Statistical Analysis

In treatment 1, the peak thoracic accelerations over the seven RV→SVC shock strengths was compared using analysis of variance; individual differences were assessed using Duncan's multiple range test. The RV→SVC peak accelerations of the seven shock strengths of treatment 1 was compared to those of treatment 2 using Bonferroni multiple-comparisons-corrected two-tailed, paired Student's t tests. The peak accelerations of treatments 2–4 were compared using analysis of variance. In treatment 2, the accelerations among the six electrode configurations was compared. The accelerations of treatments 2–4 was also compared. Lastly, two-tailed paired Student's t tests were used to compare the accelerations of the extra 100 V RV→SVC shocks delivered between treatments 1 and 2, 2 and 3, and 2 and 4. Differences in acceleration were considered significant if the p-value (P) was P<0.05.

Results

Figure 12:
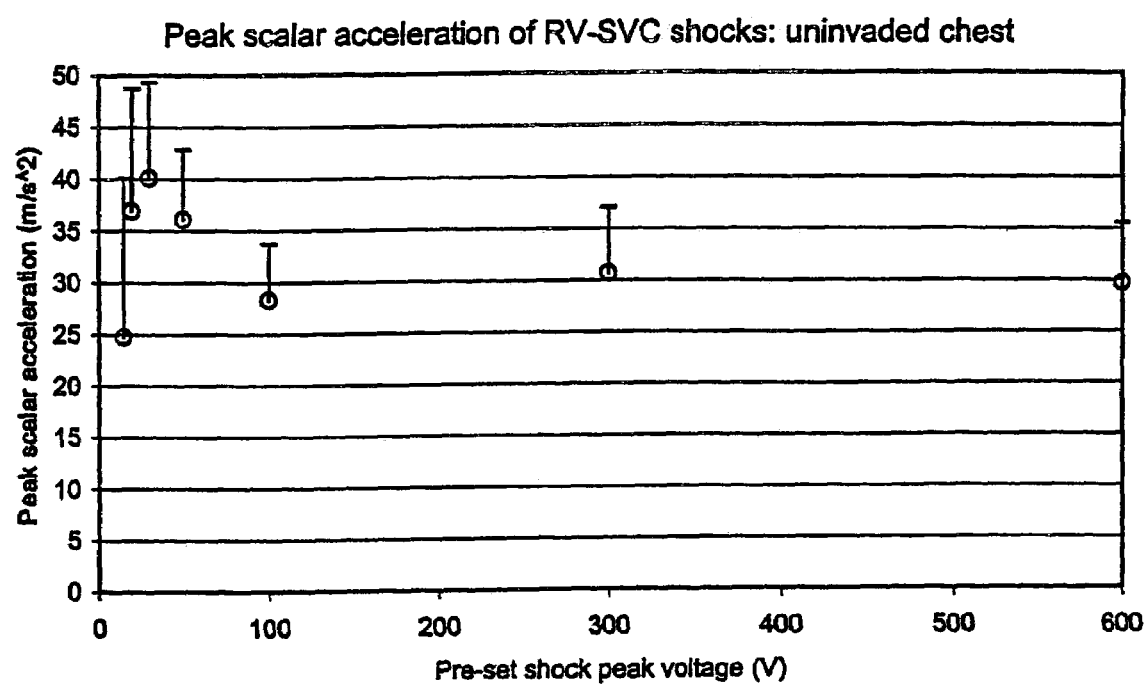
FIG. 12 is a graph of the peak scalar acceleration of shocks ($m/s^2$) in an uninvaded chest cavity according to embodiments of the invention.

All six animals completed the experimental protocol. FIGS. 11A–E shows an example of the three-dimensional thoracic accelerations measured as a result of a defibrillation shock. The mean and standard deviation of peak scalar thoracic accelerations for the RV→SVC shocks in the uninvaded chest (treatment 1) are shown in FIG. 12. Statistical trends were established differentiating the responses of the 15 V shocks to those of 20 V, 30 V, and 50 V (0.05<P<0.10), but the high standard deviation and relatively small number of subjects precluded establishing differences that were statistically significant. Likewise, trends (0.05<P<0.10) in differences were established between the responses of 20 V, 30 V and 50 V shocks to those of 100 V, 300 V, and 600 V.

Figure 13:
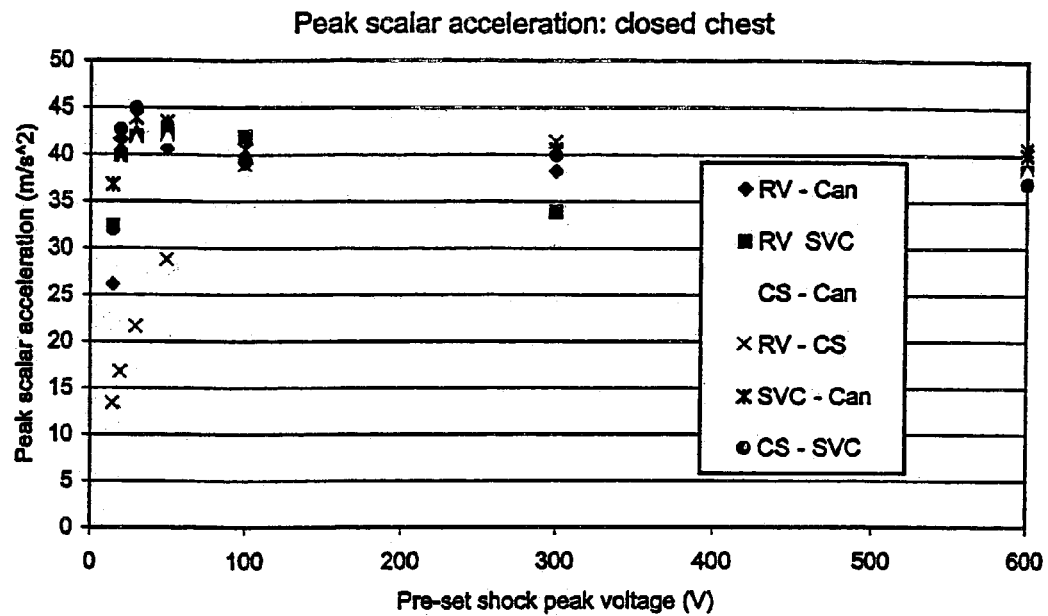
FIG. 13 is a graph of the peak scalar acceleration in an open-and-then-closed chest cavity according to embodiments of the invention.
Figure 14:
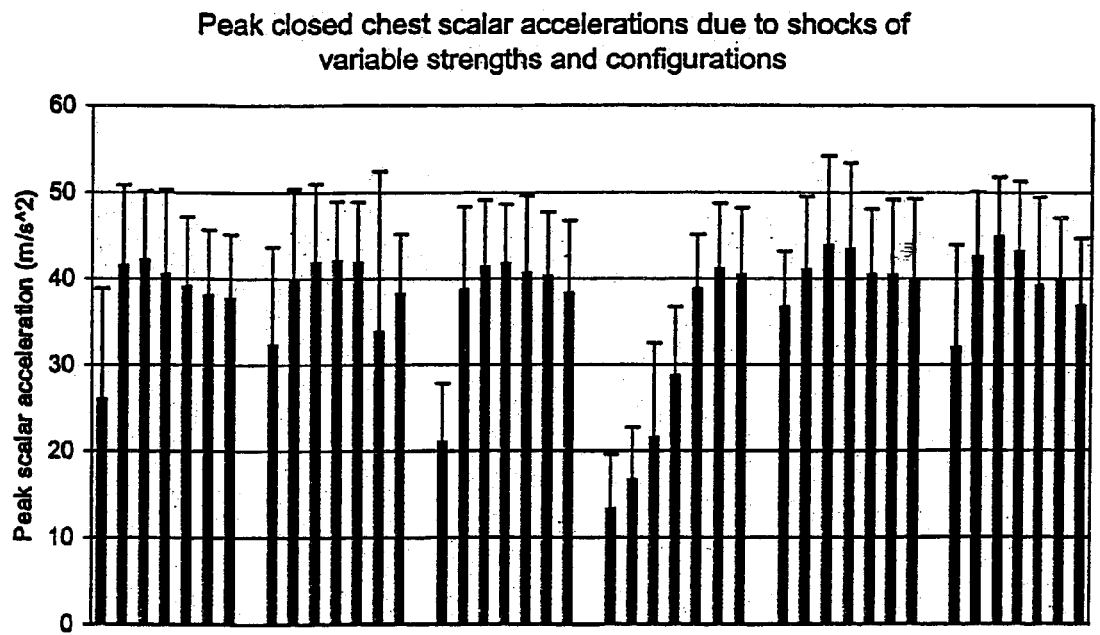
FIG. 14 is a graph of peak scalar acceleration in a closed chest cavity due to shocks of various strengths and configurations according to embodiments of the invention.

FIG. 13 shows the means of the peak scalar thoracic accelerations due to the shocks after opening and reapproximating the chest (treatment 2). FIG. 14 shows these same data along with the standard deviation of these measures. In FIG. 14, the six groups of data represent the six defibrillation configurations, in the order left-to-right of the symbols top-to-bottom in FIG. 13; the seven bars in each configuration represent the results of the 15 V, 20 V, 30 V, 50 V, 100 V, 300 V, and 600 V shocks (shown left-to-right in each group, respectively). The peak scalar accelerations of the RV→SVC shocks of 15, 100, 300, and 600 V of treatment 2 trended higher than those of treatment 1 (0.05<P<0.10). The accelerations of the shocks of 15, 20, 30, V of the RV→CS configuration in treatment 2 were significantly smaller than those of each of the other five test configurations. The accelerations of the 50 V RV→CS shocks in treatment 2 were significantly smaller than those of the RV→SVC, SVC→Can, and CS→SVC configurations (marginally so: 0.01<P<0.05), but not so for those shocks of the RV→Can and CS→Can configurations (though there was a trend so: 0.05<P<0.10).

Figure 15:
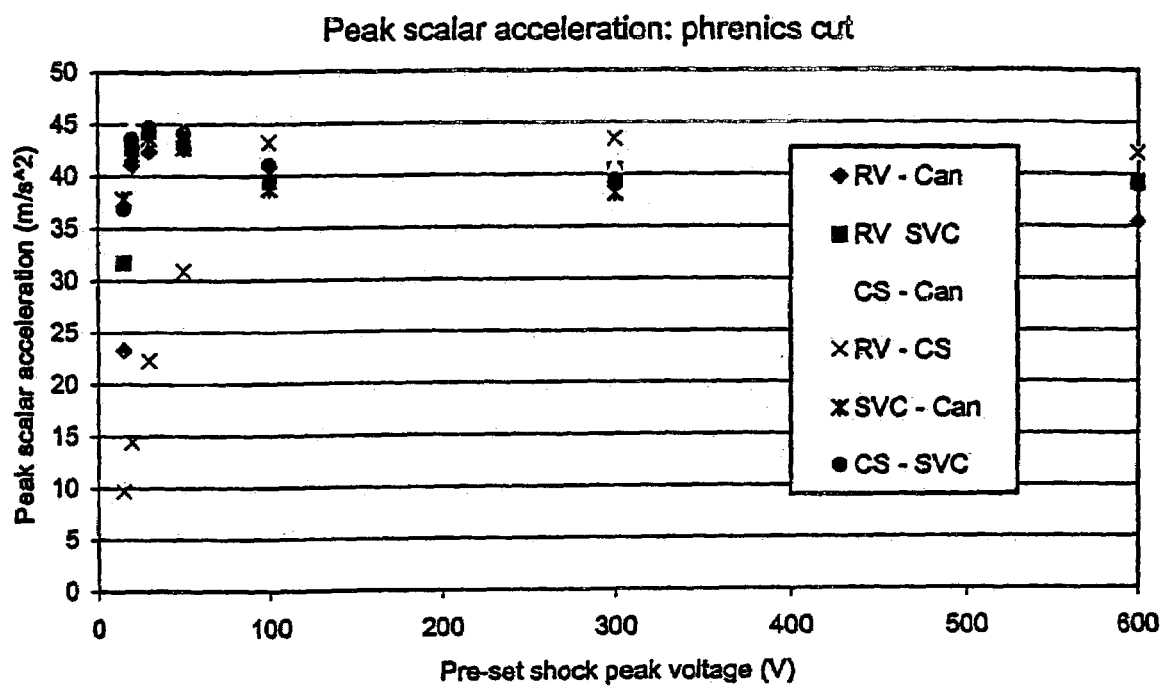
FIG. 15 is a graph of peak scalar acceleration in a subject where the phrenic nerves have been cut according to embodiments of the invention.

After re-opening the chest, incising the phrenic nerves and reapproximating the chest (treatment 3), no significant differences were found on the resulting peak scalar thoracic accelerations (see FIG. 15) compared to those of treatment 2. Like within treatment 2, the accelerations of the 15 V, 20 V, and 30 V RV→CS shocks were significantly smaller than those of the other five test configurations; differently, however, those of the 50 V RV→CS shocks were smaller than those of all of the other configurations.

Figure 16:
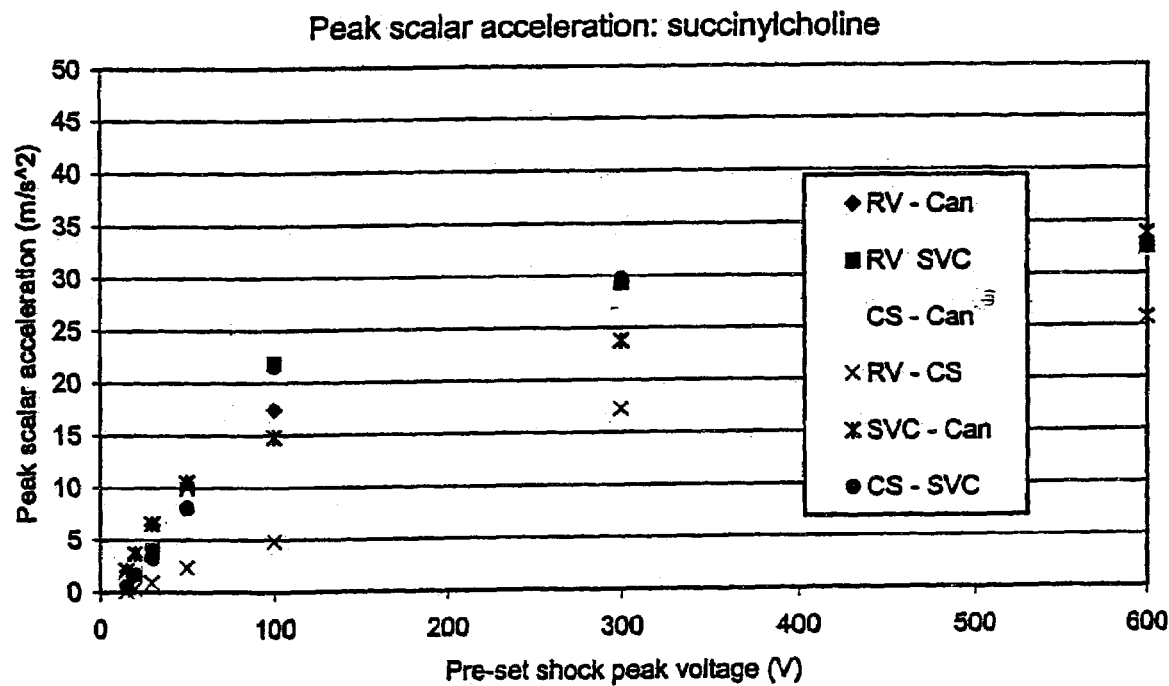
FIG. 16 is a graph of peak scalar acceleration after the delivery of a bolus and maintenance administration of succinylcholine chloride according to embodiments of the invention.

The administration of a saturating dose of the neuromuscular blocker succinylcholine chloride (treatment 4) had a profound effect on the shock-induced thoracic accelerations (see FIG. 16). Across all of the test configurations, these accelerations were significantly reduced compared to treatment 2 for shocks of 15, 20, 30, 50, and 100 V by 95±1, 94±1, 88±3, 76±10, and 57±15%, respectively (all P<0.05). The responses of shocks of 300 V and 600 V were decreased by 34±16 and 17±15%, respectively, but not significantly so.

Tables 2 and 3 show the mean and standard deviation of the absolute reduction and the percent reduction, respectively, in peak scalar thoracic acceleration of treatment 4 compared to treatment 2 for each of the six test configurations. These data indicate that the reduction profiles in thoracic acceleration over the various strength shocks were not similar across test configurations. Indeed, the accelerations resulting from shocks of the RV→CS configuration were diminished less by the neuro-muscular blocker than for the other test configurations for the smaller shocks, but more so for the larger shocks; in terms of the percent reduction, however, the reduction by the neuro-muscular blocker was greater for shocks of the RV→CS configuration than for those of the other configurations.

trend appeared to change (FIG. 18C); these data were 33±25, 38±21, 36±14, 35±17, 33±19, 40±18, and 35±15 ms, respectively.

Without wishing to be bound by a single theory, the results of the above described data from the examples may be analyzed and interpreted as follows.

The data and experimental protocol involves introducing shock-induced thoracic acceleration as an animal model for defibrillation shock discomfort. The study characterizes the thoracic acceleration undergone by anesthetized pigs to ICD-based defibrillation shocks (configurations employing RV, SVC, CS, and Can electrodes) of various amplitudes and electrode configurations, under conditions of full neural innervation, incised phrenic nerves, and complete neuro-

TABLE 2

Mean and standard deviation of the reduction in peak scalar thoracic acceleration (in m/s$^2$) after the administration of a saturating dose of succinylcholine chloride (treatment 3) relative to closed chest (treatment 1).

| Test Configuration | Shock peak voltage (v) | | | | | | |
|---|---|---|---|---|---|---|---|
| | 15 | 20 | 30 | 50 | 100 | 300 | 600 |
| RV → Can | 24 ± 13 | 39 ± 9 | 36 ± 9 | 31 ± 11 | 22 ± 11 | 9 ± 10 | 5 ± 10 |
| RV → SVC | 31 ± 12 | 38 ± 11 | 38 ± 10 | 32 ± 9 | 13 ± 19 | 12 ± 9 | 6 ± 8 |
| CS → Can | 19 ± 6 | 36 ± 9 | 35 ± 9 | 26 ± 18 | 28 ± 7 | 14 ± 7 | 6 ± 9 |
| RV → CS | 13 ± 6 | 16 ± 6 | 21 ± 11 | 26 ± 9 | 34 ± 8 | 24 ± 7 | 15 ± 4 |
| SVC → Can | 35 ± 6 | 37 ± 8 | 37 ± 9 | 33 ± 11 | 26 ± 8 | 17 ± 12 | 6 ± 10 |
| CS → SVC | 31 ± 12 | 41 ± 7 | 42 ± 7 | 35 ± 9 | 18 ± 12 | 10 ± 6 | 4 ± 9 |

TABLE 3

Mean and standard deviation of the percent reduction in peak scalar thoracic acceleration after the administration of a saturation dose of succinylcholine chloride (treatment 3) relative to closed chest (treatment 1).

| Test Configuration | Shock peak voltage (v) | | | | | | |
|---|---|---|---|---|---|---|---|
| | 15 | 20 | 30 | 50 | 100 | 300 | 600 |
| RV → Can | 91 ± 3 | 92 ± 3 | 84 ± 6 | 75 ± 13 | 52 ± 22 | 20 ± 23 | 10 ± 27 |
| RV → SVC | 97 ± 3 | 95 ± 3 | 90 ± 4 | 75 ± 8 | 46 ± 19 | 26 ± 19 | 14 ± 19 |
| CS → Can | 92 ± 2 | 92 ± 2 | 85 ± 7 | 76 ± 10 | 71 ± 17 | 35 ± 16 | 13 ± 25 |
| RV → CS | 99 ± 2 | 98 ± 3 | 95 ± 2 | 91 ± 7 | 87 ± 6 | 58 ± 11 | 36 ± 8 |
| SVC → Can | 94 ± 0 | 91 ± 1 | 85 ± 2 | 74 ± 11 | 83 ± 11 | 37 ± 26 | 11 ± 30 |
| CS → SVC | 93 ± 2 | 96 ± 1 | 93 ± 2 | 81 ± 5 | 41 ± 21 | 24 ± 14 | 9 ± 23 |

Figure 17:
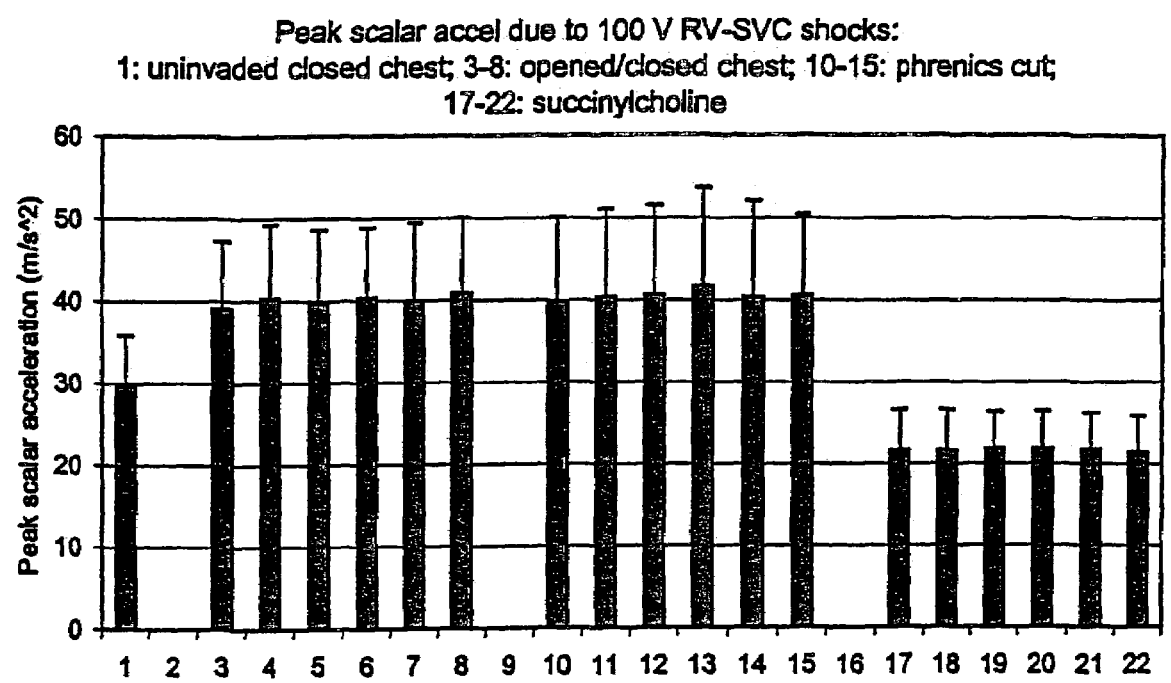
FIG. 17 is a graph of peak scalar acceleration of shocks at a fixed voltage under various clinical conditions according to embodiments of the invention.

FIG. 17 shows the peak scalar thoracic accelerations due to the extra 100 V RV→SVC shocks delivered after each test configuration throughout the experiment. The accelerations of treatment 1 were significantly lower than those of treatment 2; the accelerations of treatment 3 were not significantly different from those of treatment 2; and those of treatment 4 were significantly smaller than those of treatment 2.

Figure 18A:
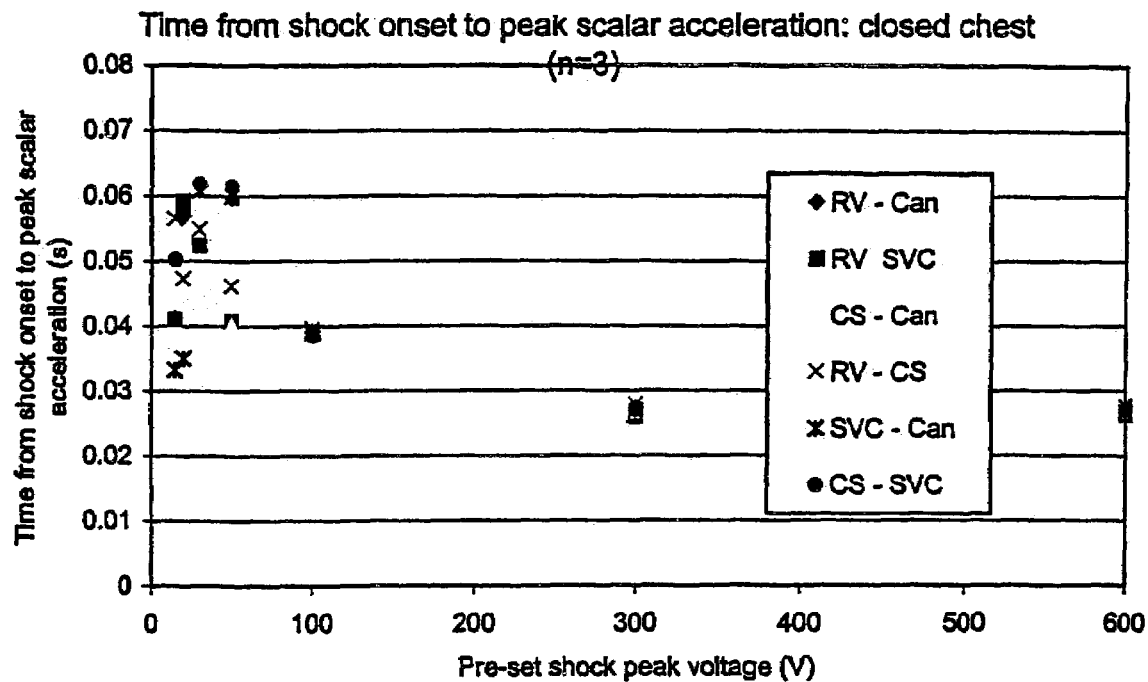
FIGS. 18A–18C are graphs of the time from the shock onset to peak acceleration according to embodiments of the invention.
Figure 18B:
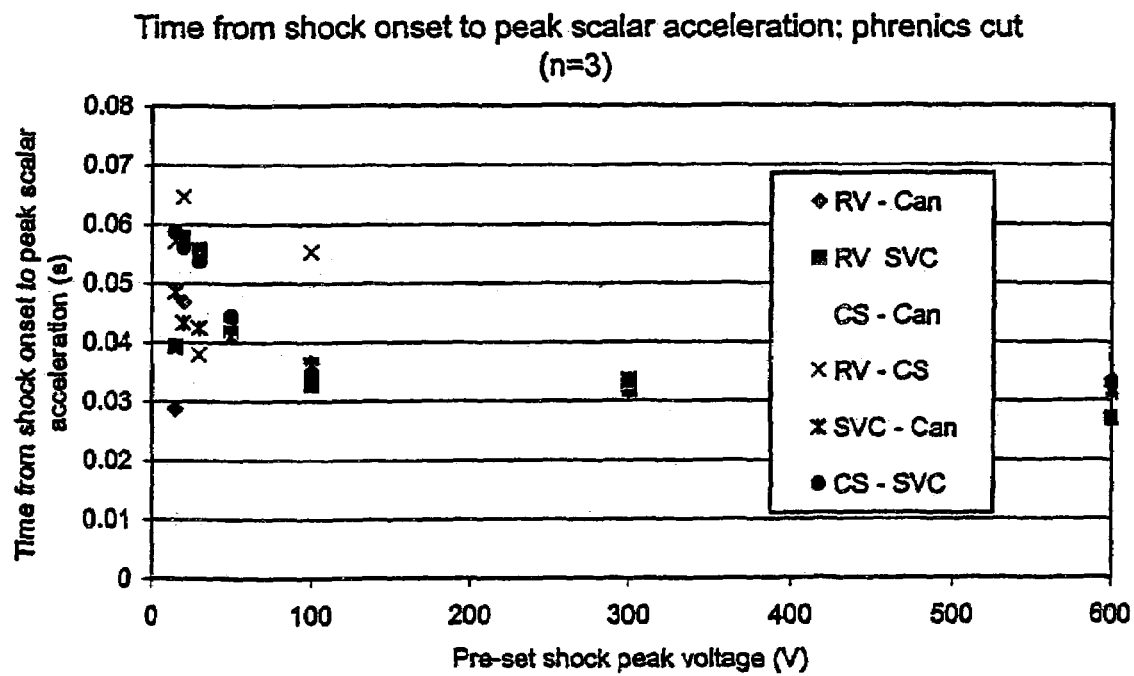
Figure 18C:
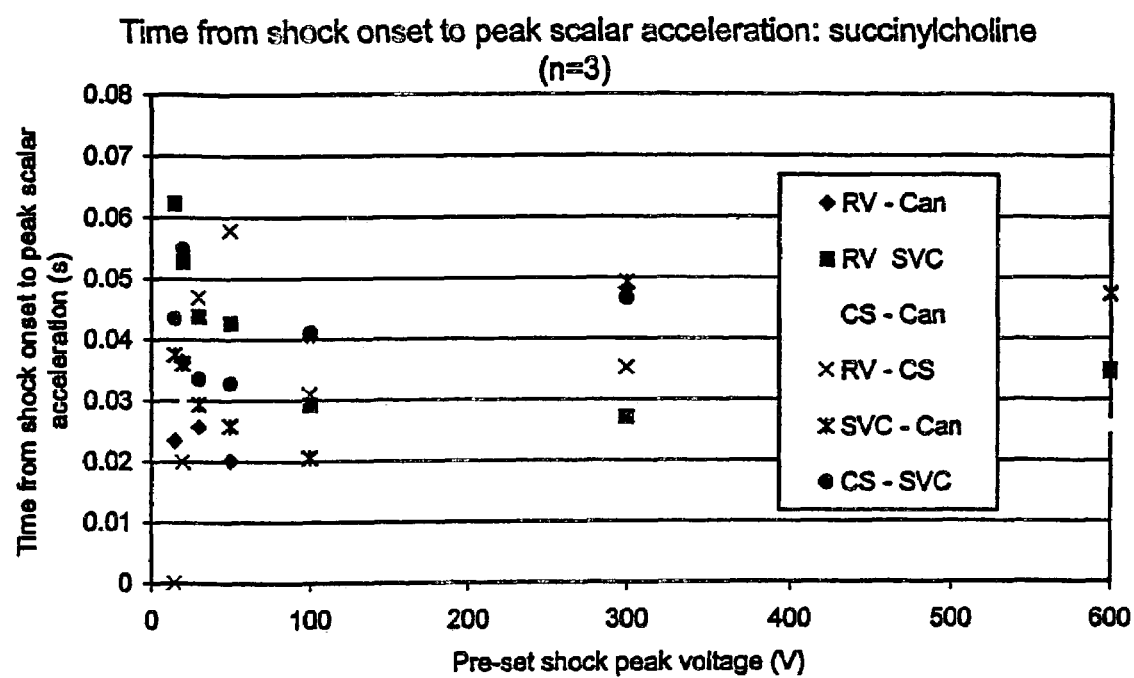

FIGS. 18A–18C show the times between the shock onset and the peak scalar thoracic acceleration for treatments 2–4, respectively. In treatment 2 (FIG. 18A), the mean and standard deviation of times between shock onset and the peak accelerations for the shocks of 15, 20, 30, 50, 100, 300, and 600 V of all of the test configurations were 43±19, 51±14, 56±28, 51±32, 39±16, 27±4, and 27±3 ms, respectively. Qualitatively, the trend of longer times for smaller shocks does not appear to change after incising the phrenic nerves (FIG. 18B); these data were 45±17, 54±12, 50±10, 42±16, 39±14, 33±13, and 32±11 ms, respectively. After administration of succynilcholine chloride, however, this muscular block. It was found that, for configurations employing an SVC or Can electrode, the peak scalar thoracic acceleration monotonically increased for shocks up to only 30 V to 50 V; for larger shocks, all the way up to 600 V, the net peak scalar acceleration did not. Shocks of the RV→CS configuration, the lone configuration tested not employing a SVC or Can electrode, elicited lesser peak thoracic accelerations than all of the other configurations. This was especially true for shocks of less than or equal to 100 V. It was also discovered that, while phrenic nerve viability did not affect the extent of shock-induced thoracic acceleration, neuro-muscular transmission did: with full neuro-muscular block, thoracic acceleration was markedly decreased, especially so for shocks of ≦100 V; for larger shocks, thoracic acceleration was only slightly, insignificantly, decreased.

The peak scalar thoracic acceleration response profiles (i.e. as a function of increasing shock strength) for all configuration treatments with intact neuro-muscular communication indicate that the acceleration reaches a plateau at shock voltages that are below the atrial defibrillation thresholds of typical catheter-based defibrillation configurations. To the extent that this experimental measure models human clinical shock discomfort, this would indicate that, for shocks to be relatively free of discomfort, they would need to be less than a few tens of volts, i.e., under about 50 V.

It appears that one possible interpretation of the data is that shocks of relatively small amplitude stimulate a discrete set of thoracic muscles through excitation of motor axons innervating these muscles, resulting in a coordinated, efficacious motion. Larger shocks, while potentially stimulating also sets of muscles through neural innervation, may also stimulate thoracic musculature directly, including possibly opposing sets of muscles, resulting in a less coordinated and efficient response.

Regarding the peak scalar thoracic acceleration profile, it is unclear if the responses are simply maintained at shock strengths above the plateau onset level of 30–50 V, or if the responses actually decrease with greater shock strengths. In treatment 1, it is arguably not possible to establish statistical significance between the responses of 20–50 V to those of 100–600 V. However, the trend was arguably clear that the responses to the larger shocks were indeed smaller than those of the shock strengths near the onset of the plateau. Such a "hump" in the response profile may be consistent with a model in which neurally stimulated thoracic muscle contraction dominates in the small shock range regime, inducing a coordinated, efficient motion, while larger shock strengths also stimulate additional thoracic musculature directly, including opposing muscle sets, resulting in a less coordinated and efficient net thoracic motion. The response profiles of treatments 2 and 3 may not have shown this hump as prominently as treatment 1 due to the extra degree of freedom of thoracic motion afforded by the opening and reapproximation of the thorax.

It has not been determined why it appears that the RV→CS configuration, at comparable shock voltages, elicited less thoracic acceleration than the other test configurations. Possibilities include: 1) the RV and CS coils were closer together than any pair of electrodes in the test system, and this configuration's shock field was naturally more confined, escaping more far-field stimulation of skeletal muscle and/or motor fiber axons than the other test configurations; 2) the RV and CS coils are more inferior than the Can and SVC electrodes, and perhaps effective neural or skeletal muscle stimulation is localized superiorly, nearer to the SVC and Can electrodes; 3) the SVC and Can electrodes are more superficial than the RV and CS electrodes; the Can is subcutaneous and supramuscular, while the SVC coil, especially the proximal end of it, extends toward the neck relatively superficially; perhaps the effective stimulation is relatively cutaneous and/or superficial.

One possible interpretation of the experimental protocol and accompanying data is that animal restraint may have affected the measured thoracic accelerations. While this may have been true to a slight extent, preliminary experimentation in which the restraint of the legs was varied could lead to the conclusion that the impact was minimal. This was likely due to how the animals were situated—on their backs along the midline of a V-shaped fluoroscopy table. Still, the legs of all of the animals were lightly restrained, primarily to keep the front hoofs from hitting the sternally situated accelerometer upon rebound after shocks. In addition, care was taken to maintain each animal in a full anterior-posterior position on the table (flatly on his back) and the additional materials of mass resting atop the animals during experimentation was not varied.

For the purpose of assessing the measurement model stability over the course of the experimental day, the responses to 100 V RV→SVC shocks were recorded after each configuration was tested in each of the three treatments. The shocks were selected a priori to be of 100 V not only because it approximates the shock strength typical for atrial defibrillation, but also because it was originally thought that it might lie along the portion of the thoracic acceleration vs. shock strength response curve that would be initially monotonically increasing. In hindsight, this latter assumption was, for the configurations tested, disproven; in actuality, the thoracic acceleration responses to RV→SVC shocks of greater than ~50 V did not vary much, and therefore the test value of 100 V may not have been optimal for assessing model stability.

To the extent that peak scalar thoracic acceleration may be a good model of patient shock discomfort, this acceleration's response profile indicates that, for typical catheter-based electrode configurations, shocks need to be less than a few tens of volts, well below the ADFTs of these configurations, for them to be well tolerated. This shock strength "discomfort threshold" may be somewhat higher for intracardiac shocks.

Also, the data may point to intracardiac shocks being less uncomfortable than shocks by electrode configurations employing extracradiac electrodes (e.g. SVC, Can). There are unfortunately scant shock discomfort studies assessing the discomfort to shock configurations employing extracradiac electrodes. One recent point of evidence, however, was reported by Neri R. Palermo P. Cesario AS. Baragli D. Amici E. Gambelli G. Internal cardioversion of chronic atrial fibrillation in patients [see comments]. Comments Comment in: Pacing Clin Electrophysiol March 1998; 21(3):633–4 Pacing & Clinical Electrophysiology. 20(9 Pt 1):2237–42, (September 1997): in a study with 22 patients, every one of them found their minimum shock strength of 180 V in an RV→SVC or RV→SVC+skin patch configuration painful or uncomfortable (Neri); for the subsequent shocks in the study, all patients received sedation. An analogous study reported in Lok N S, Lau C P, Tse H F, Ayers G M: "Clinical shock tolerability and effect of different right atrial electrode locations on efficacy of low energy human transvenous atrial defibrillation using an implantable lead system." J Am Coll Cardiol 1997;30(5): 1324–1330, also starting their testing at shocks of 180 V, but in the RA→CS configuration, found that only 3 of 27 patients requested sedation for the remainder of their study.

The present study was conducted in pigs, and it is possible that the results may not be similar in patients with AF. Also, the shocks used in this study were of fixed tilt, and therefore variable duration, depending on the shock electrode configuration; as the strength-duration relationship of shock characteristics on thoracic motion is unknown, this may have introduced some ambiguity to the results.

One possible interpretation of the data in swine is that that the peak scalar thoracic accelerations induced by ICD-based defibrillation shocks monotonically increase with shock peak voltage for most electrode configurations up to only 30–50 V, though the violence of the thoracic displacement response increased, grossly, with shock amplitude up to the maximum shock voltage tested (600 V). For shocks of up to 100 V, the peak thoracic accelerations of the RV→CS electrode configuration were significantly less than those induced by shocks of similar amplitude of all of the other five configurations tested. The distal incision of the left and right phrenic nerves did appear to not significantly affect the accelerations to shocks of any electrode configuration or shock amplitude. Lastly, it was found that application of the neuromuscular blocker succinylcholine chloride appeared to significantly reduce the thoracic accelerations due to shocks of between 15 and 100 V.

General

Systems as described above may be implanted in a patient by conventional surgical techniques, or techniques readily apparent to skilled surgeons in light of the disclosure provided herein, to provide an implanted defibrillation or cardioversion system.

Additional features can also be added to the invention without affecting the function of the invention and result thereof. Such additional features include, but are not limited to, safety features such as noise (suppression or multiple wave monitoring devices (R and T), verification checking to reduce false positive, precardioversion warning, programmed delayed intervention, bipolar configured sensing electrodes, intermittently activated defibrillation detector to reduce energy drain, a switching unit to minimize lines from the pulse generator, etc.

Although the system has been primarily described above as an implantable system, it will be appreciated by those of ordinary skill in the art that the invention could also be incorporated into an external system which employs catheters to position the electrodes within a patient's heart or other desired configuration.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of selecting a shock profile for a defibrillator based on patient discomfort to a plurality of different defibrillating shocks, comprising:
    delivering a first defibrillating shock having an associated first shock profile to a patient;
    measuring the physical displacement of a first selected region in the patient associated with the first shock during the first delivering step;
    delivering a second defibrillating shock having an associated second shock profile to the patient;
    measuring the physical displacement of a second selected region in the patient associated with the second shock during the second delivering step, wherein the second selected region is the same as or different from the first selected region; and
    selecting one of the first or second shock profiles based on which shock profile has the lesser amount of associated measured physical displacement.

2. A method according to claim 1, wherein the first and second shock profiles comprise a shock vector and waveform profile.

3. A method according to claim 1, further comprising causing the defibrillator to operate with the selected defibrillating shock profile in position in the patient.

4. A method according to claim 1, wherein the measuring steps further comprises measuring peak thoracic acceleration.

5. A method according to claim 1, wherein the measuring and delivering steps are performed over a plurality of different patients selected to provide a statistically relevant predictive population, and wherein the selecting step is based on a statistically determined lesser amount of measured physical displacement over the population.

6. A method according to claim 1, wherein the measuring, delivering, and selecting steps are individually performed on each patient to establish a customized shock profile for each respective patient to thereby reduce a patient's discomfort to administered defibrillating shocks.

7. A method according to claim 1, wherein the measuring steps comprises positioning an externally accessible 3-D accelerometer on the patient at the time of implantation and analyzing the signals generated by the accelerometer to establish the measurements.

8. A method according to claim 1, wherein the defibrillator comprises an accelerometer mounted in the implantable housing, wherein said method further comprises implanting the defibrillator in the patient, and wherein the measuring steps are carried out in vivo while the defibrillator is implanted in the patient.

9. A method according to claim 1, wherein said delivering, measuring, and selecting steps are performed to generate set-up operational parameters at initial implantation.

10. A method according to claim 1, further comprising administering an anesthetic to the patient during the delivering and measuring steps.

11. A method according to claim 1, further comprising assessing whether the selected defibrillating shock is clinically efficacious in terminating fibrillation and converting the cardiac rhythm to return to normal sinus rhythm.

12. A method according to claim 11, further comprising automatically altering the selected defibrillating shock if the shock is determined to be unsuccessful in terminating the fibrillation.

13. A method according to claim 2, wherein the first and second shock profiles differ in at least one of the shock vector and shock pulse waveform.

14. A method according to claim 1, wherein the first and second shock profiles are configured for atrial defibrillation.

15. A method according to claim 1, wherein the first and second shock profiles are configured for treating hemodynamically stable ventricular tachycardia.

16. A computer program product for assessing patient discomfort associated with selected defibrillation shocks, the computer program product comprising:
    a computer readable storage medium having computer readable program code embodied in said medium, said computer-readable program code comprising:
    computer readable program code that obtains data associated with the physical displacement of the body of a subject in response to administration of a first defibrillation shock having an associated first shock profile;
    computer readable program code that obtains data associated with the physical displacement of the body of a subject in response to administration of a second defibrillation shock having an associated second shock profile; and computer readable program code that compares the data associated with the physical displacements for the first and second shock profiles.

17. A computer program product according to claim 16, further comprising computer readable program code that selects one of the first or second shock profiles based on which shock profile has the lesser amount of measured physical displacement.

18. A computer program product according to claim 16, wherein the first and second shock profiles comprise a shock vector and waveform profile.

19. A computer program product according to claim 17, further comprising computer readable program code that causes the defibrillator to operate with the selected atrial defibrillating shock profile in position in the patient.

20. A computer program product according to claim 16, further comprising computer readable program code that measures peak thoracic acceleration.

21. A computer program product according to claim 17, further comprising computer readable program code that collects the data associated with the physical displacement of the body of a subject in response to defibrillation shocks over a plurality of different patients selected to provide a statistically relevant predictive population, and further comprising computer readable program code that selects a shock profile having a lesser amount of measured physical displacement based on a statistically determined lesser amount of measured physical displacement over the population.

22. A computer program product according to claim 17, further comprising computer readable program code that collects the data associated with the physical displacement of the body of a subject in response to defibrillation shocks individually on each patient to establish a customized shock profile for each respective patient to thereby reduce a patient's discomfort to administered defibrillation shocks.

23. A computer program product according to claim 17, wherein the computer readable program code obtains data associated with the physical displacement of the body of a subject by analyzing the signals generated by an externally accessible 3-D accelerometer placed on the patient at the time of implantation.

24. A computer program product according to claim 17, wherein the computer program product is operatively associated with an defibrillator comprising an accelerometer mounted in the implantable housing.

25. A computer program product according to claim 17, further comprising computer readable program code that assesses whether the selected atrial defibrillating shock is clinically efficacious in terminating fibrillation and converting the cardiac rhythm to return to normal sinus rhythm.

26. A computer program product according to claim 17, further comprising computer readable program code that automatically alters the selected defibrillating shock if the shock is determined to be unsuccessful in terminating the fibrillation.

27. A computer program product according to claim 18, wherein the first and second shock profiles differ in at least one of the shock vector and shock pulse waveform.

28. A defibrillator comprising:
an implantable housing;
a power source held in the housing;
a controller held in the housing operatively associated with the power source;
a shock generator held in the housing operatively associated with the power source and the controller, the shock generator being configured to deliver a plurality of different selectable shock profiles, each having a respective predetermined shock strength, waveform, and shock vector;

computer readable program code operatively associated with the controller for determining body displacement to estimate patient discomfort during the delivery of selected defibrillating shock profiles; and computer readable program code operatively associated with the controller and the shock generator for selectively delivering a selected defibrillation shock profile that is associated with a reduced body displacement value for a particular patient to thereby reduce patient discomfort during use of the defibrillator in an individualized manner.

29. A defibrillator according to claim 28, wherein the plurality of shock profiles comprise at least a first shock profile and a second shock profile and wherein the computer readable program code further comprises:

computer readable program code that obtains data associated with the physical displacement of the body of a subject in response to administration of a first defibrillation shock associated with the first shock profile;

computer readable program code that obtains data associated with the physical displacement of the body of a subject in response to administration of a second defibrillation shock associated with the second shock profile; and computer readable program code that compares the data associated with the physical displacements for the first and second shocks.

30. A defibrillator according to claim 28, wherein the computer readable program code further comprises computer readable program code that selects one of the first or second shock profiles based on which shock profile has the lesser amount of measured physical displacement.

31. A defibrillator according to claim 28, wherein the plurality of shock profiles comprises a shock vector and waveform profile.

32. A defibrillator according to claim 28, wherein the computer readable program code further comprises computer readable program code that causes the defibrillator to operate with the selected atrial defibrillating shock profile in position in the patient.

33. A defibrillator according to claim 28, wherein the computer readable program code further comprises computer readable program code that measures peak thoracic acceleration.

34. A defibrillator according to claim 28, wherein the computer readable program code further comprises:

computer readable program code that collects the data associated with the physical displacement of the body of a subject in response to defibrillation shocks over a plurality of different patients selected to provide a statistically relevant predictive population; and computer readable program code that selects a shock profile having a lesser amount of measured physical displacement based on a statistically determined lesser amount of measured physical displacement over the population.

35. A defibrillator according to claim 28, wherein the computer readable program code further comprises computer readable program code that collects the data associated with the physical displacement of the body of a subject in response to defibrillation shocks individually on each patient to establish a customized shock profile for each respective patient to thereby reduce a patient's discomfort to administered defibrillation shocks.

36. A defibrillator according to claim 28, wherein the computer readable program code further comprises computer readable program code that obtains data associated with the physical displacement of the body of a subject by analyzing the signals generated by an externally accessible 3-D accelerometer placed on the patient at the time of implantation.

37. A defibrillator according to claim 28, wherein the computer readable program code further comprises computer readable program code that assesses whether the selected atrial defibrillating shock is clinically efficacious in terminating fibrillation and converting the cardiac rhythm to return to normal sinus rhythm.

38. A defibrillator according to claim 28, wherein the computer readable program code further comprises computer readable program code that automatically alters the selected defibrillating shock if the shock is determined to be unsuccessful in terminating the fibrillation.

39. A defibrillator according to claim 28, wherein the plurality of shock profiles differ in at least one of the shock vector and shock pulse waveform.

40. A system for analyzing patient discomfort to defibrillation shocks, comprising:
  a processor;
  means for measuring physical displacement of a selected region a patient during the delivery of an defibrillation shock to estimate patient discomfort;
  means for selecting a defibrillation shock pulse for operational output to a patient that provides reduced discomfort based on measured physical displacement data;
  means for selecting an defibrillation shock pulse for operational output to a patient that is clinically efficacious and provides reduced discomfort based on measured physical displacement data.

41. A system according to claim 40, wherein the means for measuring physical displacement is an accelerometer.

42. A system according to claim 40, wherein the means for selecting comprises a computer readable program code for comparing the physical displacement associated with a first shock profile and the physical displacement associated with a second shock profile and selecting one of the first or second shock profiles based on which shock profile has the lesser amount of associated measured physical displacement.

* * * * *